(12) United States Patent
Stad et al.

(10) Patent No.: US 7,918,858 B2
(45) Date of Patent: Apr. 5, 2011

(54) MINIMALLY INVASIVE BONE ANCHOR EXTENSIONS

(75) Inventors: Shawn D. Stad, Fall River, MA (US); Christopher Ramsay, New Bedford, MA (US); Brian Fergus Murphy, Co. Clare (IE)

(73) Assignee: DePuy Spine, Inc., Raynham, MA (US)

( * ) Notice: Subject to any disclaimer, the term of this patent is extended or adjusted under 35 U.S.C. 154(b) by 458 days.

(21) Appl. No.: 11/539,504

(22) Filed: Oct. 6, 2006

(65) Prior Publication Data

US 2008/0077135 A1 Mar. 27, 2008

Related U.S. Application Data

(60) Provisional application No. 60/827,000, filed on Sep. 26, 2006.

(51) Int. Cl.
*A61F 5/00* (2006.01)
(52) U.S. Cl. .......................... 606/86 A; 606/279; 606/99
(58) Field of Classification Search .............. 606/86 A, 606/86 R, 99, 104, 246, 279; 81/442, 444, 81/451–455; 135/114, 120.1–120.3, 907; 294/100
See application file for complete search history.

(56) References Cited

U.S. PATENT DOCUMENTS

| | | | |
|---|---|---|---|
| 522,747 A | 7/1894 | Waldenberger | |
| 604,250 A | 5/1898 | Jocelyn | |
| 1,311,147 A | 7/1919 | Brentsen | |
| 1,492,466 A * | 4/1924 | Jarmolowsky | 81/112 |
| 2,005,955 A | 6/1935 | Renouf | |
| 2,248,054 A | 7/1941 | Becker | |
| 2,268,576 A | 1/1942 | Drewett | |
| 2,320,709 A | 6/1943 | Arnesen | |
| 2,346,346 A | 4/1944 | Anderson | |
| 2,514,589 A | 7/1950 | Penman | |
| 2,548,729 A | 4/1951 | Kumpman | |
| 2,684,168 A | 7/1954 | McGinnis et al. | |
| 3,224,799 A | 12/1965 | Blose et al. | |
| 3,246,646 A | 4/1966 | Murphy | |

(Continued)

FOREIGN PATENT DOCUMENTS

DE 2649042 B1 1/1978

(Continued)

OTHER PUBLICATIONS

Office Action dated Jun. 23, 2009 in U.S. Appl. No. 11/539,504.

(Continued)

*Primary Examiner* — Eduardo C Robert
*Assistant Examiner* — Steven J Cotroneo
(74) *Attorney, Agent, or Firm* — Nutter McClennen & Fish LLP

(57) ABSTRACT

Methods and devices are provided for facilitating delivery and implanting of a bone anchor into bone. In one exemplary embodiment, a bone anchor extension is provided for coupling to a bone anchor to facilitate delivery and implanting of the bone anchor in bone. The bone anchor extension can have a generally elongate configuration that allows it to extend from a skin incision in a patient to a site proximate a patient's spine, and it can include a lumen extending therethrough between proximal and distal ends thereof. A distal end of the bone anchor extension can be adapted to engage a bone anchor, such as a bone screw. Various techniques are provided for locking the distal end of the bone anchor extension into engagement with a bone anchor.

21 Claims, 19 Drawing Sheets

U.S. PATENT DOCUMENTS

| | | |
|---|---|---|
| 3,552,799 A | 1/1971 | Koranda |
| 3,997,138 A | 12/1976 | Crock et al. |
| 4,041,636 A | 8/1977 | Folker |
| 4,263,899 A | 4/1981 | Burgin |
| 4,274,401 A | 6/1981 | Miskew |
| 4,324,036 A | 4/1982 | Reilly |
| 4,369,011 A | 1/1983 | Ploss |
| 4,373,754 A | 2/1983 | Bollfrass et al. |
| 4,382,438 A | 5/1983 | Jacobs |
| 4,461,281 A | 7/1984 | Carson |
| 4,492,749 A | 1/1985 | Scheler |
| 4,537,448 A | 8/1985 | Ketterer |
| 4,545,374 A | 10/1985 | Jacobson |
| 4,573,448 A | 3/1986 | Kambin |
| 4,611,580 A | 9/1986 | Wu |
| 4,686,966 A | 8/1987 | Tsai |
| 4,759,241 A | 7/1988 | Voswinkel |
| 4,763,644 A | 8/1988 | Webb |
| 4,765,311 A | 8/1988 | Kulik et al. |
| 4,799,372 A | 1/1989 | Marcon et al. |
| 4,805,602 A | 2/1989 | Puno et al. |
| 4,815,453 A | 3/1989 | Cotrel |
| 4,836,196 A | 6/1989 | Park et al. |
| 4,848,368 A | 7/1989 | Kronner |
| 4,864,614 A | 9/1989 | Crowther |
| 4,872,451 A | 10/1989 | Moore et al. |
| 4,887,020 A | 12/1989 | Graham |
| 4,887,596 A | 12/1989 | Sherman |
| 4,913,134 A | 4/1990 | Luque |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,015,255 A | 5/1991 | Kuslich |
| 5,024,659 A | 6/1991 | Sjostrom |
| 5,042,982 A | 8/1991 | Harms et al. |
| 5,052,372 A | 10/1991 | Shapiro |
| 5,052,643 A | 10/1991 | Law |
| 5,067,955 A | 11/1991 | Cotrel |
| 5,084,053 A | 1/1992 | Ender |
| 5,092,635 A | 3/1992 | DeLange et al. |
| 5,092,867 A | 3/1992 | Harms et al. |
| 5,092,893 A | 3/1992 | Smith |
| 5,129,388 A | 7/1992 | Vignaud et al. |
| 5,154,719 A | 10/1992 | Cotrel |
| 5,171,279 A | 12/1992 | Mathews |
| 5,176,680 A | 1/1993 | Vignaud et al. |
| 5,196,013 A | 3/1993 | Harms et al. |
| 5,207,678 A | 5/1993 | Harms et al. |
| 5,217,497 A | 6/1993 | Mehdian |
| 5,231,973 A | 8/1993 | Dickie |
| 5,242,443 A | 9/1993 | Kambin |
| 5,242,446 A | 9/1993 | Steffee et al. |
| 5,261,907 A | 11/1993 | Vignaud et al. |
| 5,261,912 A | 11/1993 | Frigg |
| 5,261,913 A | 11/1993 | Marnay |
| 5,282,862 A | 2/1994 | Baker et al. |
| 5,282,863 A | 2/1994 | Burton |
| 5,324,290 A | 6/1994 | Zdeblick et al. |
| 5,352,231 A | 10/1994 | Brumfield et al. |
| 5,357,983 A | 10/1994 | Mathews |
| 5,360,431 A | 11/1994 | Puno et al. |
| 5,367,983 A | 11/1994 | Pound et al. |
| 5,385,583 A | 1/1995 | Cotrel |
| 5,395,317 A | 3/1995 | Kambin |
| 5,397,363 A | 3/1995 | Gelbard |
| 5,429,639 A | 7/1995 | Judet |
| 5,439,464 A | 8/1995 | Shapiro |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,484,440 A | 1/1996 | Allard |
| 5,496,321 A | 3/1996 | Puno et al. |
| 5,505,690 A | 4/1996 | Patton et al. |
| 5,509,922 A | 4/1996 | Aranyi et al. |
| 5,520,610 A | 5/1996 | Giglio et al. |
| 5,520,689 A | 5/1996 | Schlapfer et al. |
| 5,536,268 A | 7/1996 | Griss |
| 5,545,165 A | 8/1996 | Biedermann et al. |
| 5,554,157 A | 9/1996 | Errico et al. |
| 5,569,248 A | 10/1996 | Mathews |
| 5,584,887 A | 12/1996 | Kambin |
| 5,585,020 A | 12/1996 | Becker et al. |
| 5,586,984 A | 12/1996 | Errico et al. |
| 5,589,901 A | 12/1996 | Means |
| 5,605,457 A | 2/1997 | Bailey et al. |
| 5,647,873 A | 7/1997 | Errico et al. |
| 5,651,789 A | 7/1997 | Cotrel |
| 5,667,508 A | 9/1997 | Errico et al. |
| 5,669,911 A | 9/1997 | Errico et al. |
| 5,672,176 A | 9/1997 | Biedermann et al. |
| 5,680,963 A | 10/1997 | Brusko et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,716,356 A | 2/1998 | Biedermann et al. |
| 5,725,527 A | 3/1998 | Biedermann et al. |
| 5,728,097 A | 3/1998 | Mathews |
| 5,733,286 A | 3/1998 | Errico et al. |
| 5,738,685 A | 4/1998 | Halm et al. |
| 5,741,261 A | 4/1998 | Moskovitz et al. |
| 5,749,884 A | 5/1998 | Benderev et al. |
| 5,762,629 A | 6/1998 | Kambin |
| 5,766,221 A | 6/1998 | Benderev et al. |
| 5,782,833 A | 7/1998 | Haider |
| 5,788,097 A | 8/1998 | McInnes |
| 5,797,911 A | 8/1998 | Sherman et al. |
| 5,810,818 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,879,350 A | 3/1999 | Sherman et al. |
| 5,882,350 A | 3/1999 | Ralph et al. |
| 5,885,286 A | 3/1999 | Sherman et al. |
| 5,888,221 A | 3/1999 | Gelbard |
| 5,891,145 A | 4/1999 | Morrison et al. |
| 5,891,147 A | 4/1999 | Moskovitz et al. |
| 5,897,590 A | 4/1999 | Donovan |
| 5,899,904 A | 5/1999 | Errico et al. |
| 5,899,905 A | 5/1999 | Errico et al. |
| 5,910,141 A | 6/1999 | Morrison et al. |
| 5,925,047 A | 7/1999 | Errico et al. |
| 5,928,139 A | 7/1999 | Koros et al. |
| 5,931,777 A | 8/1999 | Sava |
| 5,947,969 A | 9/1999 | Errico et al. |
| 5,954,635 A | 9/1999 | Foley et al. |
| 5,961,266 A | 10/1999 | Tseng |
| 5,964,760 A | 10/1999 | Richelsoph |
| 5,976,146 A | 11/1999 | Ogawa et al. |
| 5,984,922 A | 11/1999 | McKay |
| 5,984,923 A | 11/1999 | Breard |
| 5,989,254 A | 11/1999 | Katz |
| 6,004,349 A | 12/1999 | Jackson |
| 6,010,503 A | 1/2000 | Richelsoph et al. |
| 6,033,406 A | 3/2000 | Mathews |
| 6,053,917 A | 4/2000 | Sherman et al. |
| 6,056,753 A | 5/2000 | Jackson |
| 6,059,786 A | 5/2000 | Jackson |
| 6,074,391 A | 6/2000 | Metz-Stavenhagen et al. |
| 6,077,262 A | 6/2000 | Schlapfer et al. |
| 6,083,225 A | 7/2000 | Winslow et al. |
| 6,083,227 A | 7/2000 | Saurat et al. |
| 6,090,110 A | 7/2000 | Metz-Stavenhagen |
| 6,099,528 A | 8/2000 | Saurat et al. |
| 6,102,912 A | 8/2000 | Cazin et al. |
| 6,102,913 A | 8/2000 | Jackson |
| 6,113,602 A | 9/2000 | Sand |
| 6,120,760 A | 9/2000 | Hotten et al. |
| 6,132,431 A | 10/2000 | Nilsson et al. |
| 6,132,432 A | 10/2000 | Richelsoph |
| 6,139,493 A | 10/2000 | Koros et al. |
| 6,139,549 A | 10/2000 | Keller |
| 6,139,551 A | 10/2000 | Michelson et al. |
| 6,159,179 A | 12/2000 | Simonson |
| 6,183,472 B1 | 2/2001 | Lutz et al. |
| 6,200,322 B1 | 3/2001 | Branch et al. |

| | | | | | | |
|---|---|---|---|---|---|---|
| RE37,161 E | 5/2001 | Michelson et al. | | 7,179,261 B2 | 2/2007 | Sicvol et al. |
| 6,224,545 B1 | 5/2001 | Cocchia et al. | | 7,250,052 B2 | 7/2007 | Landry et al. |
| 6,224,598 B1 | 5/2001 | Jackson | | 7,306,603 B2 | 12/2007 | Boehm, Jr. et al. |
| 6,226,548 B1 | 5/2001 | Foley et al. | | 7,527,638 B2 | 5/2009 | Anderson et al. |
| 6,235,028 B1 | 5/2001 | Brumfield et al. | | 7,666,188 B2 | 2/2010 | Anderson et al. |
| 6,251,112 B1 | 6/2001 | Jackson | | 2001/0001119 A1 | 5/2001 | Lombardo |
| 6,254,602 B1 | 7/2001 | Justis | | 2001/0010000 A1 | 7/2001 | Gertzbein et al. |
| 6,258,090 B1 | 7/2001 | Jackson | | 2001/0023350 A1 | 9/2001 | Choi |
| 6,261,287 B1 | 7/2001 | Metz-Stavenhagen | | 2001/0025180 A1 | 9/2001 | Jackson |
| 6,280,442 B1 | 8/2001 | Barker et al. | | 2001/0034521 A1 | 10/2001 | Bailey et al. |
| 6,296,642 B1 | 10/2001 | Morrison et al. | | 2002/0007183 A1 | 1/2002 | Lee et al. |
| 6,299,616 B1 | 10/2001 | Beger | | 2002/0010467 A1 | 1/2002 | Cooper et al. |
| 6,302,633 B1 | 10/2001 | Poe | | 2002/0011600 A1 | 1/2002 | Kurahashi et al. |
| 6,315,564 B1 | 11/2001 | Levisman | | 2002/0013585 A1 | 1/2002 | Gournay et al. |
| 6,331,179 B1 | 12/2001 | Freid et al. | | 2002/0022842 A1 | 2/2002 | Horvath et al. |
| 6,355,040 B1 | 3/2002 | Richelsoph et al. | | 2002/0026192 A1 | 2/2002 | Schmiel et al. |
| 6,358,254 B1 | 3/2002 | Anderson | | 2002/0026193 A1 | 2/2002 | Barker et al. |
| 6,361,535 B2 | 3/2002 | Jackson | | 2002/0032443 A1 | 3/2002 | Sherman et al. |
| 6,368,321 B1 | 4/2002 | Jackson | | 2002/0035366 A1 | 3/2002 | Walder et al. |
| 6,371,968 B1 | 4/2002 | Kogasaka et al. | | 2002/0040243 A1 | 4/2002 | Attali et al. |
| 6,371,989 B1 | 4/2002 | Chauvin et al. | | 2002/0045898 A1 | 4/2002 | Freid et al. |
| 6,379,356 B1 | 4/2002 | Jackson | | 2002/0049368 A1 | 4/2002 | Ritland |
| 6,387,097 B1 | 5/2002 | Alby | | 2002/0049444 A1 | 4/2002 | Knox |
| 6,416,515 B1 | 7/2002 | Wagner | | 2002/0055739 A1 | 5/2002 | Lieberman |
| 6,428,541 B1 | 8/2002 | Boyd et al. | | 2002/0058942 A1 | 5/2002 | Biedermann et al. |
| 6,440,132 B1 | 8/2002 | Jackson | | 2002/0068938 A1 | 6/2002 | Jackson |
| 6,440,133 B1 * | 8/2002 | Beale et al. ............... 606/86 A | | 2002/0068940 A1 | 6/2002 | Gaines |
| 6,440,137 B1 | 8/2002 | Horvath et al. | | 2002/0068975 A1 | 6/2002 | Teitelbaum et al. |
| 6,443,953 B1 | 9/2002 | Perra et al. | | 2002/0082598 A1 | 6/2002 | Teitelbaum |
| 6,454,768 B1 | 9/2002 | Jackson | | 2002/0082600 A1 | 6/2002 | Shaolian et al. |
| 6,454,772 B1 | 9/2002 | Jackson | | 2002/0082602 A1 | 6/2002 | Biedermann et al. |
| 6,458,131 B1 | 10/2002 | Ray | | 2002/0091386 A1 | 7/2002 | Martin et al. |
| 6,458,132 B2 | 10/2002 | Choi et al. | | 2002/0095153 A1 | 7/2002 | Jones et al. |
| 6,468,276 B1 | 10/2002 | McKay | | 2002/0111626 A1 | 8/2002 | Ralph et al. |
| 6,471,705 B1 | 10/2002 | Biedermann et al. | | 2002/0111628 A1 | 8/2002 | Ralph et al. |
| 6,475,218 B2 | 11/2002 | Gournay et al. | | 2002/0116000 A1 | 8/2002 | Zucherman et al. |
| 6,485,220 B2 | 11/2002 | Hecht | | 2002/0116001 A1 | 8/2002 | Schafer et al. |
| 6,485,491 B1 | 11/2002 | Farris et al. | | 2002/0116006 A1 | 8/2002 | Cohen |
| 6,485,518 B1 | 11/2002 | Cornwall et al. | | 2002/0120272 A1 | 8/2002 | Yuan et al. |
| 6,487,798 B2 | 12/2002 | Sueshige | | 2002/0123668 A1 | 9/2002 | Ritland |
| 6,488,681 B2 | 12/2002 | Martin et al. | | 2002/0133154 A1 | 9/2002 | Saint Martin |
| 6,488,682 B2 | 12/2002 | Kikuchi et al. | | 2002/0138076 A1 | 9/2002 | Biedermann et al. |
| 6,488,683 B2 | 12/2002 | Lieberman | | 2002/0138077 A1 | 9/2002 | Ferree |
| 6,520,907 B1 | 2/2003 | Foley et al. | | 2002/0143341 A1 | 10/2002 | Biedermann et al. |
| 6,520,990 B1 | 2/2003 | Ray | | 2002/0161368 A1 | 10/2002 | Foley et al. |
| 6,524,315 B1 | 2/2003 | Selvitelli et al. | | 2002/0169448 A1 | 11/2002 | Vanacker |
| 6,530,028 B1 | 3/2003 | Yokoyama | | 2002/0169450 A1 | 11/2002 | Lange |
| 6,530,926 B1 | 3/2003 | Davison | | 2002/0173791 A1 | 11/2002 | Howland |
| 6,530,929 B1 | 3/2003 | Justis et al. | | 2002/0183747 A1 | 12/2002 | Jao et al. |
| 6,537,276 B2 | 3/2003 | Metz-Stavenhagen et al. | | 2002/0183748 A1 | 12/2002 | Martin et al. |
| 6,540,748 B2 | 4/2003 | Lombardo | | 2002/0183749 A1 | 12/2002 | Burgess et al. |
| 6,540,749 B2 | 4/2003 | Schafer et al. | | 2002/0188295 A1 | 12/2002 | Martz et al. |
| 6,554,831 B1 | 4/2003 | Rivard et al. | | 2002/0198526 A1 | 12/2002 | Shaolian et al. |
| 6,554,834 B1 | 4/2003 | Crozet et al. | | 2003/0004511 A1 | 1/2003 | Ferree |
| 6,607,530 B1 | 8/2003 | Carl et al. | | 2003/0004512 A1 | 1/2003 | Farris et al. |
| 6,641,586 B2 | 11/2003 | Varieur | | 2003/0009168 A1 | 1/2003 | Beale et al. |
| 6,648,888 B1 | 11/2003 | Shluzas | | 2003/0023240 A1 | 1/2003 | Amrein et al. |
| 6,652,527 B2 | 11/2003 | Zucherman et al. | | 2003/0023243 A1 | 1/2003 | Biedermann et al. |
| 6,660,006 B2 | 12/2003 | Markworth et al. | | 2003/0028190 A1 | 2/2003 | Patel et al. |
| 6,666,891 B2 | 12/2003 | Boehm, Jr. et al. | | 2003/0032957 A1 | 2/2003 | McKinley |
| 6,723,100 B2 | 4/2004 | Biedermann et al. | | 2003/0045875 A1 | 3/2003 | Bertranou et al. |
| 6,726,689 B2 | 4/2004 | Jackson | | 2003/0045879 A1 | 3/2003 | Minfelde et al. |
| 6,730,089 B2 | 5/2004 | Jackson | | 2003/0050640 A1 | 3/2003 | Lee et al. |
| 6,740,086 B2 | 5/2004 | Richelsoph | | 2003/0055426 A1 | 3/2003 | Carbone et al. |
| 6,740,089 B2 | 5/2004 | Haider | | 2003/0055427 A1 | 3/2003 | Graf |
| 6,743,231 B1 | 6/2004 | Gray et al. | | 2003/0060823 A1 | 3/2003 | Bryan |
| 6,755,829 B1 | 6/2004 | Bono et al. | | 2003/0060824 A1 | 3/2003 | Viart et al. |
| 6,793,656 B1 | 9/2004 | Mathews | | 2003/0060826 A1 | 3/2003 | Foley et al. |
| 6,821,277 B2 | 11/2004 | Teitelbaum | | 2003/0083657 A1 | 5/2003 | Drewry et al. |
| 6,837,889 B2 | 1/2005 | Shluzas | | 2003/0083688 A1 | 5/2003 | Simonson |
| 6,849,064 B2 | 2/2005 | Hamada | | 2003/0083689 A1 | 5/2003 | Simonson |
| 6,905,500 B2 | 6/2005 | Jeon et al. | | 2003/0100896 A1 | 5/2003 | Biedermann et al. |
| 6,911,030 B1 | 6/2005 | Vanacker et al. | | 2003/0100904 A1 | 5/2003 | Biedermann |
| 6,929,647 B2 | 8/2005 | Cohen | | 2003/0130659 A1 | 7/2003 | Haider |
| 7,081,117 B2 | 7/2006 | Bono et al. | | 2003/0191371 A1 | 10/2003 | Smith et al. |
| 7,083,621 B2 | 8/2006 | Shaolian et al. | | 2003/0195549 A1 | 10/2003 | Davison et al. |
| 7,125,426 B2 | 10/2006 | Moumene et al. | | 2003/0195550 A1 | 10/2003 | Davison et al. |
| 7,156,850 B2 | 1/2007 | Kim | | 2003/0195551 A1 | 10/2003 | Davison et al. |
| 7,179,225 B2 | 2/2007 | Shluzas et al. | | 2003/0199885 A1 | 10/2003 | Davison et al. |

| | | | |
|---|---|---|---|
| 2003/0199916 A1 | 10/2003 | Yee et al. | |
| 2003/0208203 A1 | 11/2003 | Lim et al. | |
| 2003/0216748 A1 | 11/2003 | Gitis et al. | |
| 2003/0216768 A1 | 11/2003 | Gitis et al. | |
| 2003/0225408 A1* | 12/2003 | Nichols et al. | 606/61 |
| 2003/0229347 A1 | 12/2003 | Sherman et al. | |
| 2004/0006301 A1 | 1/2004 | Sell et al. | |
| 2004/0039384 A1 | 2/2004 | Boehm et al. | |
| 2004/0082961 A1 | 4/2004 | Teitelbaum | |
| 2004/0138662 A1 | 7/2004 | Landry et al. | |
| 2004/0143265 A1 | 7/2004 | Landry et al. | |
| 2004/0147937 A1* | 7/2004 | Dunbar et al. | 606/99 |
| 2004/0162560 A1 | 8/2004 | Raynor et al. | |
| 2004/0172022 A1 | 9/2004 | Landry et al. | |
| 2004/0181224 A1 | 9/2004 | Biedermann et al. | |
| 2004/0204711 A1 | 10/2004 | Jackson | |
| 2004/0243139 A1 | 12/2004 | Lewis et al. | |
| 2004/0260284 A1 | 12/2004 | Parker | |
| 2004/0267277 A1 | 12/2004 | Zannis et al. | |
| 2005/0001022 A1 | 1/2005 | Fieser | |
| 2005/0011383 A1 | 1/2005 | Hadden | |
| 2005/0033299 A1 | 2/2005 | Shluzas | |
| 2005/0038432 A1 | 2/2005 | Shaolian et al. | |
| 2005/0038434 A1 | 2/2005 | Mathews | |
| 2005/0065517 A1 | 3/2005 | Chin | |
| 2005/0080418 A1 | 4/2005 | Simonson et al. | |
| 2005/0085813 A1 | 4/2005 | Spitler et al. | |
| 2005/0096748 A1 | 5/2005 | Yoon | |
| 2005/0119667 A1* | 6/2005 | Leport et al. | 606/104 |
| 2005/0131408 A1* | 6/2005 | Sicvol et al. | 606/61 |
| 2005/0131422 A1 | 6/2005 | Anderson et al. | |
| 2005/0171540 A1 | 8/2005 | Lim et al. | |
| 2005/0171549 A1 | 8/2005 | Boehm et al. | |
| 2005/0182410 A1 | 8/2005 | Jackson | |
| 2005/0192570 A1 | 9/2005 | Jackson | |
| 2005/0192571 A1 | 9/2005 | Abdelgany | |
| 2005/0192579 A1 | 9/2005 | Jackson | |
| 2006/0036255 A1 | 2/2006 | Pond et al. | |
| 2006/0079909 A1 | 4/2006 | Runco et al. | |
| 2006/0173454 A1 | 8/2006 | Spitler et al. | |
| 2007/0093849 A1* | 4/2007 | Jones et al. | 606/99 |
| 2007/0129731 A1 | 6/2007 | Sicvol et al. | |
| 2007/0233155 A1 | 10/2007 | Lovell | |

FOREIGN PATENT DOCUMENTS

| | | |
|---|---|---|
| DE | 2903342 A1 | 7/1980 |
| DE | 3434807 | 12/1985 |
| DE | 3639810 A1 | 5/1988 |
| DE | 3711013 C1 | 6/1988 |
| DE | 8915443 U1 | 6/1990 |
| DE | 9006568 U1 | 10/1990 |
| DE | 3916198 A1 | 11/1990 |
| DE | 4307576 C1 | 4/1994 |
| DE | 9403231 U1 | 4/1994 |
| DE | 29810798 U1 | 10/1999 |
| DE | 19912364 A1 | 10/2000 |
| DE | 10027988 A1 | 1/2002 |
| DE | 10136129 A1 | 2/2003 |
| DE | 10157969 C1 | 2/2003 |
| EP | 242708 A2 | 10/1987 |
| EP | 283373 A1 | 9/1988 |
| EP | 324022 A1 | 7/1989 |
| EP | 328883 A2 | 8/1989 |
| EP | 330881 A1 | 9/1989 |
| EP | 346521 A1 | 12/1989 |
| EP | 348272 A1 | 12/1989 |
| EP | 379551 A1 | 8/1990 |
| EP | 392927 A2 | 10/1990 |
| EP | 441729 A1 | 8/1991 |
| EP | 452451 A1 | 10/1991 |
| EP | 465158 A2 | 1/1992 |
| EP | 528562 A2 | 2/1993 |
| EP | 528706 A1 | 2/1993 |
| EP | 572790 A1 | 12/1993 |
| EP | 0614649 A1 | 9/1994 |
| EP | 771635 A2 | 5/1997 |
| EP | 836835 A2 | 4/1998 |
| EP | 870474 A1 | 10/1998 |
| EP | 1133951 A2 | 9/2001 |
| EP | 1190678 A2 | 3/2002 |
| EP | 1332722 A1 | 8/2003 |
| FR | 2624720 A1 | 6/1989 |
| FR | 2659546 A1 | 9/1991 |
| FR | 2729291 A1 | 7/1996 |
| FR | 2796545 A1 | 1/2001 |
| JP | 6476847 | 3/1989 |
| WO | 8900028 A1 | 1/1989 |
| WO | 9000377 A1 | 1/1990 |
| WO | 9106254 A1 | 5/1991 |
| WO | 9116020 A1 | 10/1991 |
| WO | 9205742 A1 | 4/1992 |
| WO | 9220294 A1 | 11/1992 |
| WO | 9308745 A1 | 5/1993 |
| WO | 9311715 A1 | 6/1993 |
| WO | 9414384 A2 | 7/1994 |
| WO | 9501132 A1 | 1/1995 |
| WO | 9513755 A1 | 5/1995 |
| WO | 9513756 A1 | 5/1995 |
| WO | 9514437 A1 | 6/1995 |
| WO | 9812977 A1 | 4/1998 |
| WO | 0027297 | 5/2000 |
| WO | 0101873 A1 | 1/2001 |
| WO | 02069854 A1 | 9/2002 |
| WO | 2004004100 A1 | 1/2004 |
| WO | 2004017847 A2 | 3/2004 |
| WO | 2004041100 A1 | 5/2004 |
| WO | 2005041799 A1 | 5/2005 |

OTHER PUBLICATIONS

"CD Horizon Legacy 5.5 Spinal System" Brochure, Medtronic Sofamor Danek, USA Inc., 2003.

DePuy AcroMed Product Brochure "rnicro'TLIF, A Mini-Open and Intermuscular Transforaminal Lumbar Interbody Fusion" Aperture Spinal System, (22 pages) Oct. 2002.

Ebara et al; A New System For The Anterio Restoration and Fixation of Thoracic Spinal Deformities Using an Andoscopic Approach; Spine 200 Apr. 1;pp. 876-83; vol. 25(7).

Foley, Kevin T., "CD Horizon SEXTANT Rod Insertion System Surgical Technique" Medtronic Sofamor Danek Product Brochure (32 pages) Jul. 2002.

Glazer et al.; Biomechanical analysis of Multilevel Fixation Methods in the Lumbar Spine; Spine Jan. 15, 1997; pp. 171-182;vol. 22(2).

Jampel, Robert and Charles Bloomgarden. "Individual extraocular muscle function from faradic stimulation of the oculomotor and trochlear nerves of the macaque," Investigative Opthamology, Jun. 1963, 265-266.

Jeanneret, Posterior Rod System of the Cervical Spine: A New Implant Allowing Optimal Screw Insertion, Eur. Spine J 1996; pp. 350-356, 5(5):Springer-Verlag.

John R. Walker, "Machining Fundamentals Fundamental Basic to Industry", The Goodheart-Wilcox Co., Inc., 1981, pp. 2,179-186, including redacted version.

Kaneda et al; New Anterior Instrumentation For the Management of Thoracolumbar and Lumbar Scoliosis; Spine May 15, 1996; pp. 1250-1261; vol. 21(10).

Lascoe et al., "Machineshop—Operations and Setups", American Technical Society, 1973, pp. 380, 386 and 388 including redacted version.

Ltr to Robert Malone from Dept of Health & Human Services, Jun. 20, 2002 regarding Forex Corporation OPTIMA• Devices 510(k) Summary, 5 pages.

Muller, et al., "A Keyhole Approach for Endoscopically Assisted Pedicle Screw Fixation in Lumbar Spine Instability," Neurosurgery, vol. 47, No. 1, Jul. 2000.

OPTIMAa Spinal system Surgical Technique Brochure, pp. 1-17.

Search Report from related EP 04 81 2446 dated Dec. 2, 2008.

Shapiro et al.; Spinal Instrumentation With a Low Complication Rate; Surg. Neurol. Dec. 1997; pp. 566-574; vol. 48(6) Elsevier Science.

Speer, et al., "An Arthroscopic Technique for Anterior Stabiliatin of the Shoulder with A Bioabsorbable Tack," J. Bone Joint Surg Am. 1996; 78:1801-7.

The Dilation Retractor System products literature (4 pages) Bright Medical Instruments Apr. 2001.

U&I Corporation Thoracolumbar Spine Optima Spinal System from website www.uandi.co.kr pp. 1-2 Nov. 10, 2005.

Viau et al.; Thoracic Pedicle Screw Instrumentation Using the "Funnell Technique"; J. Spinal Discord Tech. Dec. 2002; pp. 450-453; vol. 15(6).

Wiltse LL and Spencer, CW, "New Uses and Refinements of the Paraspinal Approach," Jun. 6, 1988, Lippincott Williams and Wilkins, Spine Jun. 1988;13(6):969-706.

XIA Spine System Brochure, Stryker Howmedica Osteonics, pp. 1-7, Stryker Corporation, Rutherford, NJ. Jul. 1999.

\* cited by examiner

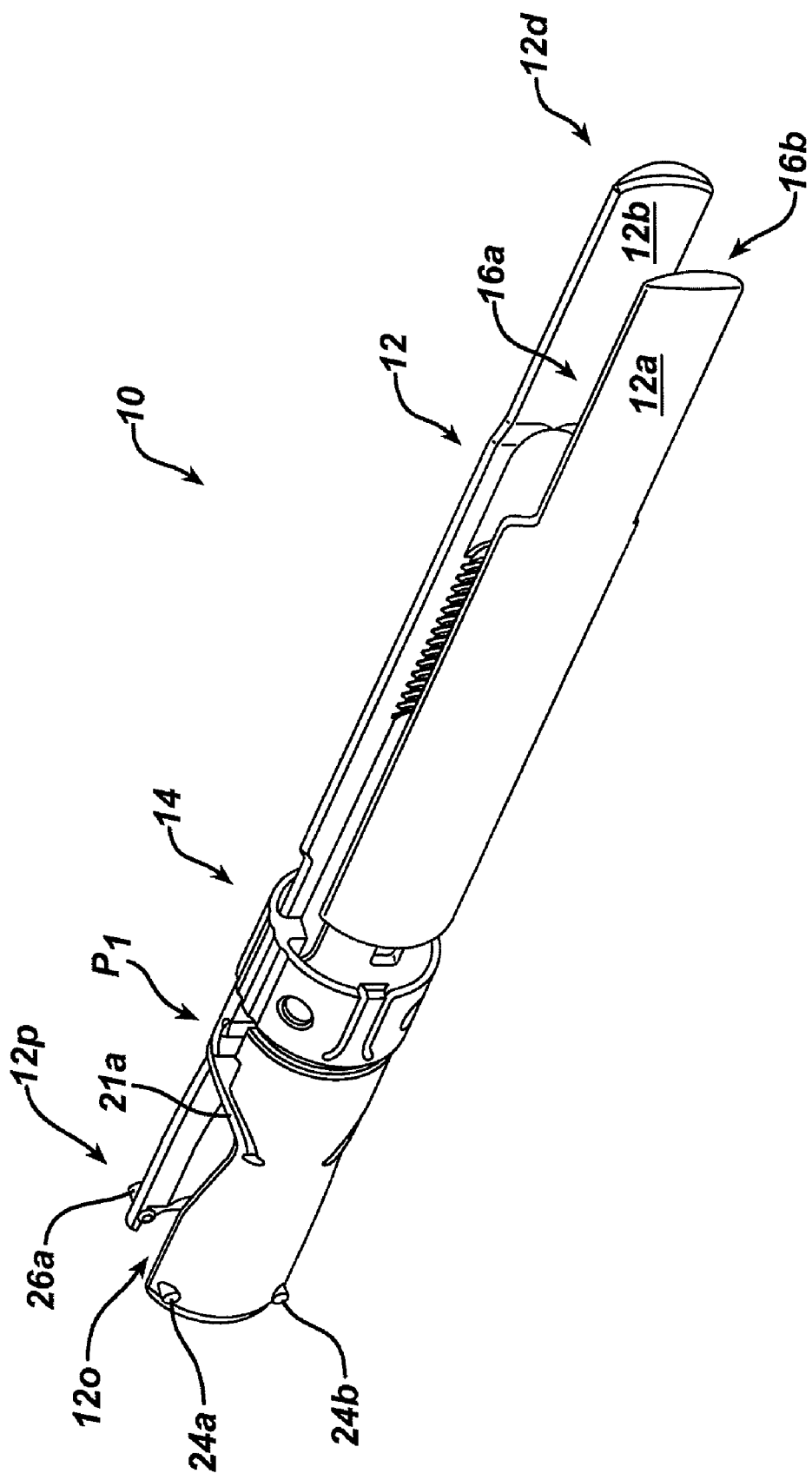

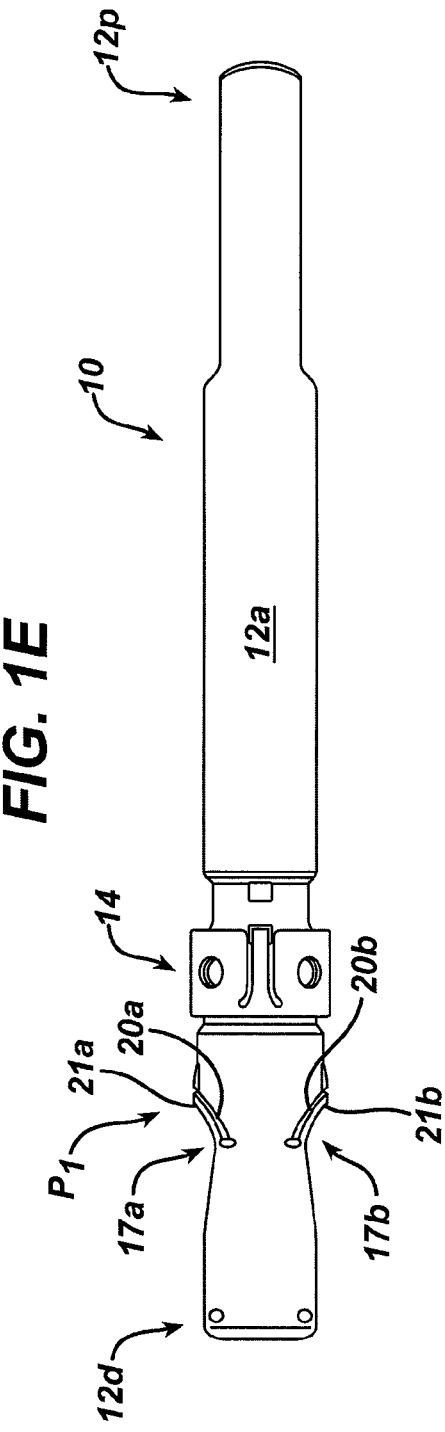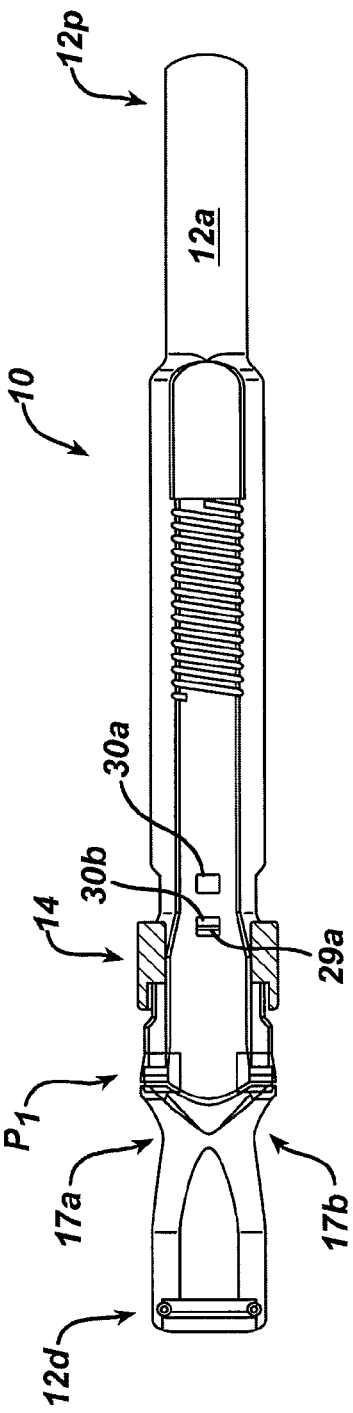

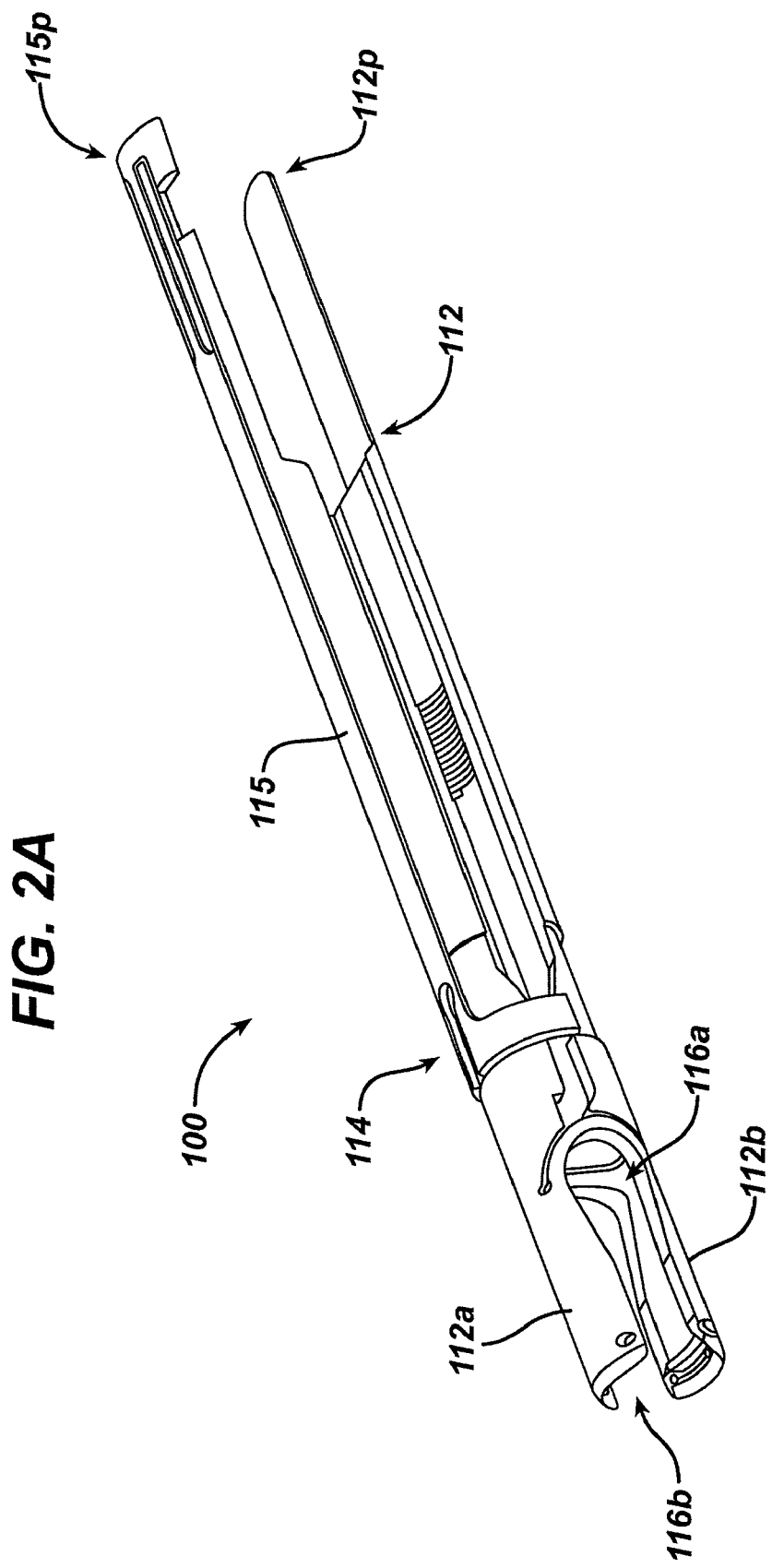

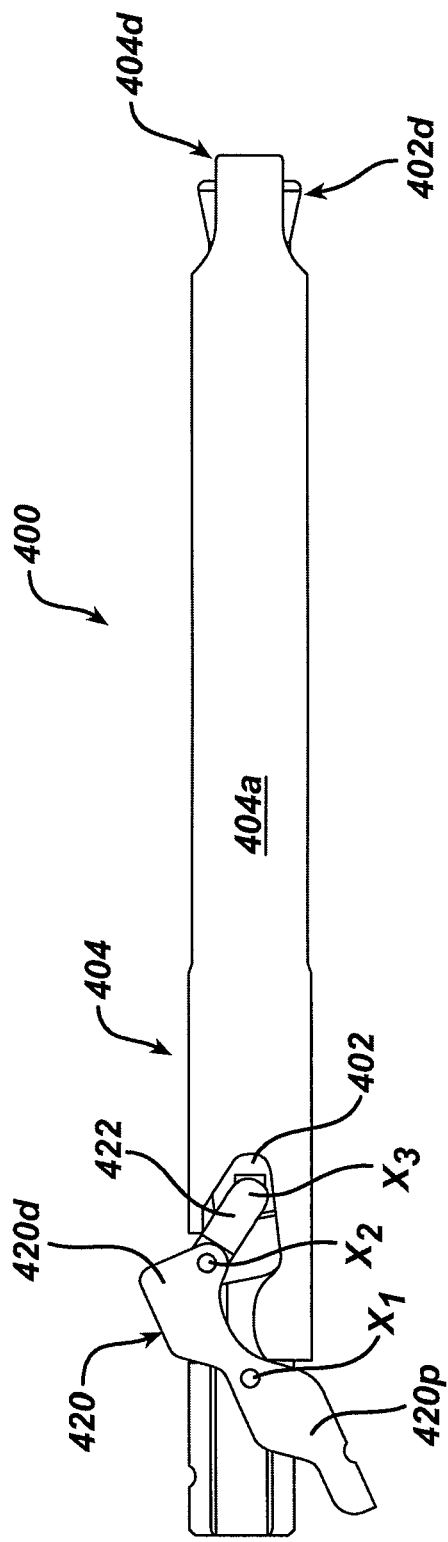
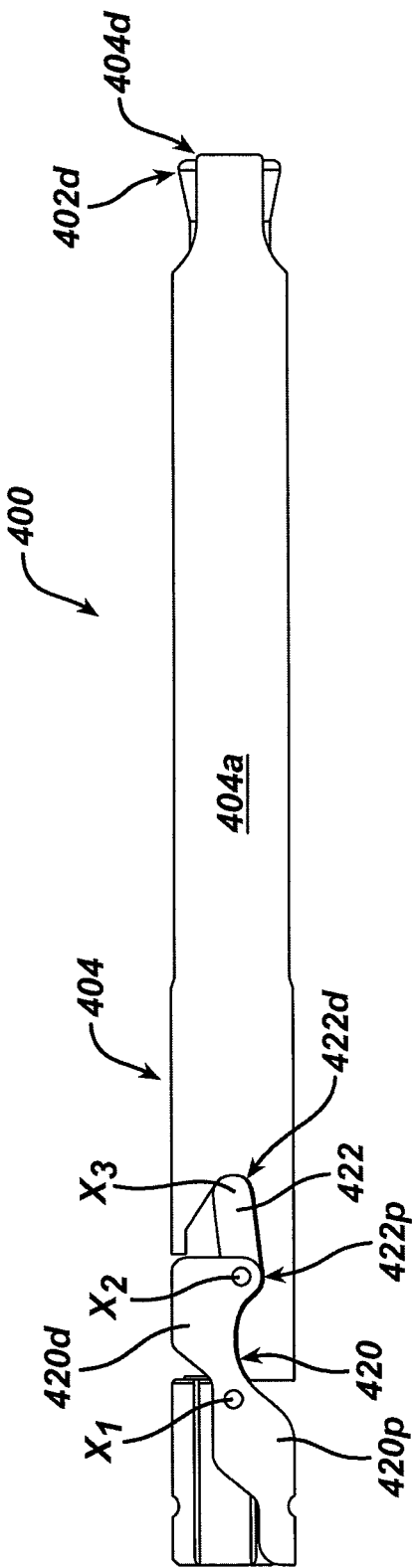

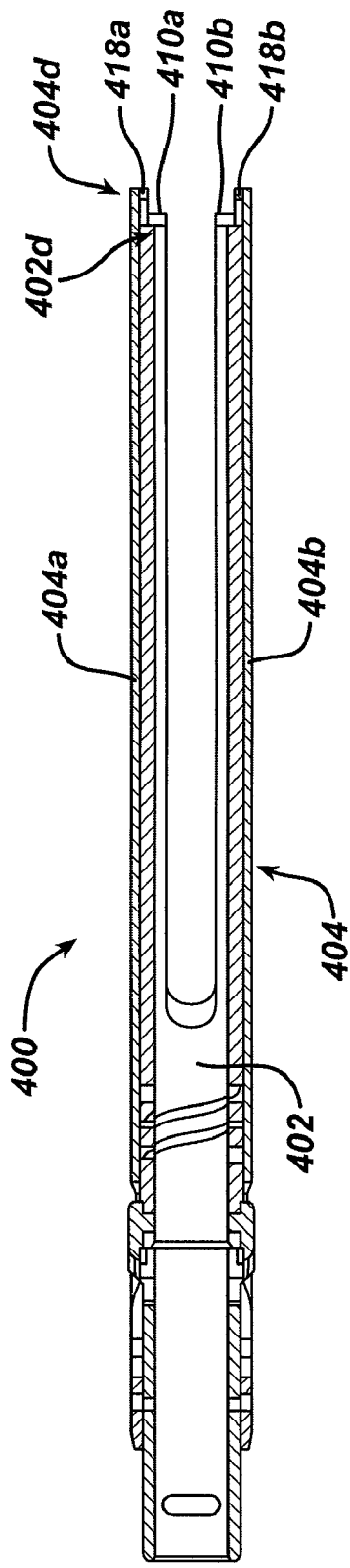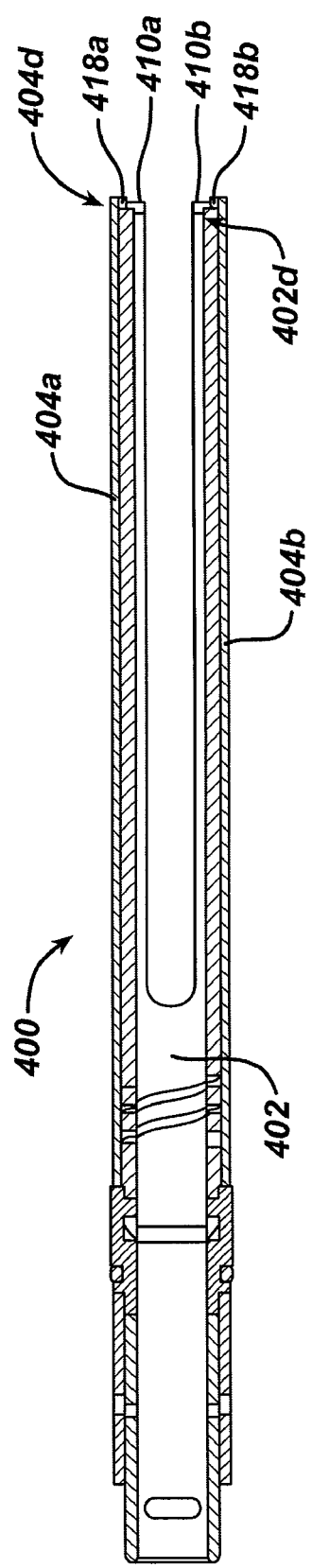

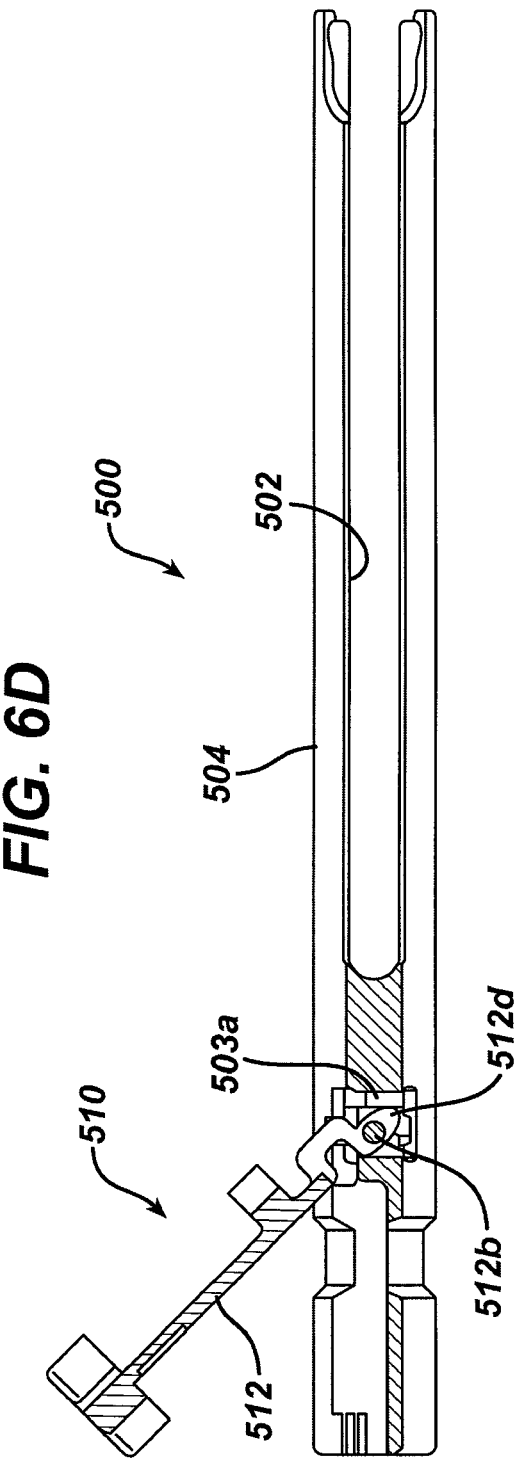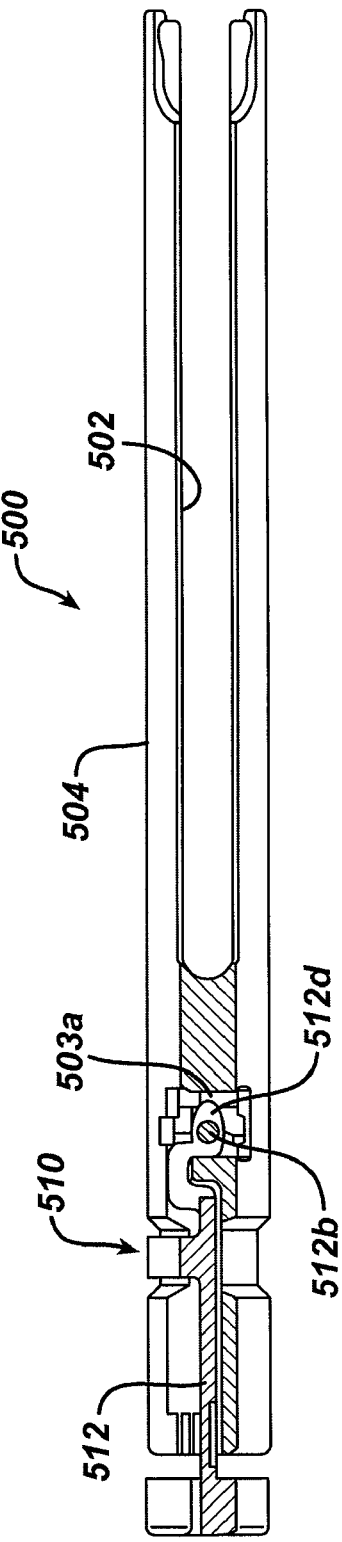

MINIMALLY INVASIVE BONE ANCHOR EXTENSIONS

CROSS-REFERENCE TO RELATED APPLICATIONS

This application claims priority to U.S. Provisional Application No. 60/827,000 filed on Sep. 26, 2006 and entitled "Minimally Invasive Bone Anchors Extensions," which is hereby incorporated by reference in its entirety.

FIELD OF THE INVENTION

The present invention relates to methods and devices for implanting bone anchors.

BACKGROUND OF THE INVENTION

For a number of known reasons, spinal fixation devices are used in orthopedic surgery to align and/or fix a desired relationship between adjacent vertebral bodies. Such devices typically include a spinal fixation element, such as a relatively rigid fixation rod or plate, that is coupled to adjacent vertebrae by attaching the element to various anchoring devices, such as hooks, bolts, wires, or screws. The fixation elements can have a predetermined contour that has been designed according to the properties of the target implantation site, and once installed, the fixation element holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped recess formed in the head. A set-screw, plug, or similar type of closure mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other closure mechanism to securely interconnect each screw and the fixation rod.

Recently, the trend in spinal surgery has been moving toward providing minimally invasive devices and methods for implanting bone anchors and spinal fixation devices.

SUMMARY OF THE INVENTION

The present invention generally provides methods and devices for implanting bone anchors and spinal fixation devices. In one embodiment, a percutaneous access device is provided having a hollow elongate member with an inner lumen extending therethrough and adapted to span from at least a skin incision in a patient to a predetermined site proximate a spine of the patient. The hollow elongate member can include opposed arms coupled by at least one fulcrum such that the opposed arms are adapted to pivot relative to one another to releasably engage a bone anchor between a distal end of the opposed arms. The device can also include a locking mechanism disposed between the opposed arms and movable between an unlocked position in which the opposed arms are free to pivot relative to one another, and a locked position in which the locking mechanism prevents the opposed arms from moving toward and away from one another to lock a bone anchor into engagement with the opposed arms.

In one embodiment, the locking mechanism can be slidably coupled to the hollow elongate member such that the locking mechanism slides proximally and distally between the unlocked and locked positions. The locking mechanism can include, for example, at least one block extending between the opposed arms and positioned proximal of the fulcrum. The block can be formed on a band at least partially disposed around the hollow elongate member. The band can have various features. For example, the band can include a retaining element formed thereon and adapted to selectively retain the band in the locked and unlocked positions. In one embodiment, the retaining element can be at least one deflectable tang formed on the band, and the hollow elongate member can include at least one opening formed therein for receiving the deflectable tang. In another embodiment, the band can include an elongate arm extending proximally therefrom and adapted to slidably move the band proximally and distally along the hollow elongate member, and/or opposed extension arms extending distally from the band and adapted to be positioned adjacent to a distal portion of the opposed arms when the block is in the locked position to prevent outward deflection of the opposed arms.

In another embodiment, the locking mechanism can be rotatably coupled to the hollow elongate member such that the locking mechanism rotates between the locked and unlocked position. For example, the locking mechanism can be a plug rotatably disposed within the hollow elongate member. The plug can have an oblong shape that includes a maximum diameter adapted to extend between the opposed arms when the plug is in the locked position to prevent pivotal movement of the opposed arms, and a minimum diameter adapted to extend between the opposed arms when the plug is in the unlocked position to allow pivotal movement of the opposed arms.

The hollow elongate member can also have a variety of configurations. In one embodiment, the hollow elongate member can include opposed first and second slots formed therein and extending proximally from a distal end of the hollow elongate member to define the opposed arms of the hollow elongate member. A first fulcrum can be disposed within the first slot and a second fulcrum can be disposed within the second slot. The opposed arms of the hollow elongate member can also include an engagement mechanism formed on a distal end thereof for engaging a bone anchor. The engagement mechanism can be, for example, a lip formed on an inner surface of each of the opposed arms and adapted to engage a corresponding groove formed in a bone screw. The distal end of the opposed arms can also include an anti-rotation mechanism formed thereon for preventing rotation of a bone anchor engaged between the opposed arms. The anti-rotation mechanism can be, for example, first and second pins extending inward from opposed outer regions of the first arm, and first and second pins extending inward from opposed outer regions of the second arm.

A spinal anchoring system is also provided and can include a bone anchor having a head with a bone-engaging shank extending therefrom, and a bone anchor extension. The bone anchor extension can include a tubular member adapted to span from at least a skin incision in a patient to a predetermined site proximate a spine of the patient. The tubular member can have first and second opposed arms and an inner lumen extending therethrough between proximal and distal ends thereof. The first and second opposed arms can include a distal end adapted to pivot relative to one another to releasably engage the head of the bone anchor. The bone anchor extension can also include a locking mechanism coupled to the tubular member and movable between an unlocked position in which the opposed arms are free to pivot relative to one another, and a locked position in which the locking mechanism is positioned between the opposed arms and prevents the opposed arms from moving toward and away from one another thereby locking the opposed arms into engagement with the head of the bone anchor. In an exemplary embodiment, the opposed arms can be pivotally coupled to one another by at least one fulcrum. The locking mechanism can be positioned proximal of the at least one fulcrum. The locking mechanism can be, for example, at least one block adapted to extend into at least one slot formed between the opposed arms when the locking mechanism is in the locked position. In another embodiment, the head of the bone anchor can include a groove formed therein, and a distal end of the opposed arms can include a lip formed on an inner surface thereof and adapted to engage the groove formed in the head to mate the bone anchor to the opposed arms.

Exemplary surgical methods are also provided, and in one embodiment the method can include positioning a head of a bone anchor between a distal end of opposed arms of an extension device. The opposed arms can pivot relative to one another to engage the head of the bone anchor. The method can also include moving a locking mechanism coupled to the extension device from an unlocked position in which the opposed arms are free to pivot relative to one another, to a locked position in which the locking mechanism extends between the opposed arms and prevents the opposed arms from pivoting relative to one another to lock the head of the bone anchor into engagement with the opposed arms. The method can also include implanting the bone anchor in bone, preferably after the bone anchor is mated to the extension device. A spinal fixation element can also be positioned within the head of the bone anchor, and a fastening element can be inserted through the extension device and mated to the head of the bone anchor to lock the spinal fixation element within the head of the bone anchor. The locking mechanism can be moved from the locked position to the unlocked position to release the head of the bone anchor from the opposed arms of the extension device. In an exemplary embodiment, the locking mechanism is positioned between a tissue surface and the bone anchor, and an actuator located above the tissue surface is actuated to move the locking mechanism. In another embodiment, moving the locking mechanism from the unlocked position to the locked position can include sliding the locking mechanism along a longitudinal axis of the extension device. For example, the locking mechanism can be slid from a proximal position to a distal position. In yet another embodiment, moving the locking mechanism from the unlocked position to the locked position can include rotating the locking mechanism relative to the extension device.

In another embodiment, a bone anchor extension is provided and includes an inner tube having proximal and distal ends with a lumen extending therebetween, and an outer tube disposed about at least a portion of the inner tube and having proximal and distal ends with a lumen extending therebetween. The outer tube is sized to span from at least a skin incision in a patient to a predetermined site proximate a spine of the patient. The bone anchor extension also includes a locking mechanism pivotally coupled to the inner and outer tubes such that pivotal movement of the locking mechanism is effective to move the inner tube relative to the outer tube to engage a bone anchor between the distal end of the inner tube and the distal end of the outer tube. In an exemplary embodiment, the locking mechanism is movable between a first position in which the locking mechanism extends longitudinally relative to a longitudinal axis of the outer tube, and a second position in which the locking mechanism extends transversely outward relative to a longitudinal axis of the outer tube. For example, the inner and outer tubes can be effective to engage and lock a bone anchor between the distal ends thereof when the locking mechanism is in the first position, and a bone anchor can be released from the distal ends of the inner and outer tubes when the locking mechanism is in the second position.

In one exemplary embodiment, the locking mechanism can include an arm pivotally coupled to the outer tube, and a linkage pivotally coupled between the arm and the inner tube such that pivotal movement of the arm relative to the outer tube is effective to pull the linkage to move the inner tube relative to the outer tube. The linkage can extend at an angle relative to a longitudinal axis of the outer tube to releasably lock the locking mechanism in the first position, and the arm can be effective to pull the linkage and inner tube in a proximal direction relative to the outer tube when the arm is moved from the first position to the second position.

In another exemplary embodiment, the locking mechanism can include an arm having at least one cam formed thereon and disposed between the inner and outer tubes. The cam can be pivotally coupled to the outer tube and disposed within at least one cut-out formed in the inner tube such that pivotal movement of the arm is effective to move the inner tube relative to the outer tube. The inner tube can include opposed cut-outs formed in the proximal end thereof, and pivotal movement of the arm between the first and second positions can be effective to alter a size of the opposed cut-outs to thereby move the inner tube relative to the outer tube. The device can also include a locking mechanism formed on at least one of the arm and the outer tube and effective to releasably lock the arm in the first position. The locking mechanism can be, for example, a plurality of teeth formed on the outer tube and adapted to engage the arm.

In other aspects, a spinal anchoring system is provided and includes a bone anchor having a head with a bone-engaging shank extending therefrom, and a bone anchor extension having an inner tube having proximal and distal ends with a lumen extending therebetween, and an outer tube disposed about at least a portion of the inner tube and having proximal and distal ends with a lumen extending therebetween. The outer tube can be sized to span from at least a skin incision in a patient to a predetermined site proximate a spine of the patient. The bone anchor extension can also include a locking mechanism pivotally coupled to at least one of the inner and outer tubes and adapted to pivot to move the inner tube relative to the outer tube to engage the head of bone anchor between the distal end of the inner tube and the distal end of the outer tube. In one embodiment, the locking mechanism can include a cam disposed between the inner and outer tubes. The cam can be disposed within a cut-out formed in the inner tube, and it can have a boss formed thereon and pivotally coupled to the outer tube. In use, the cam can be adapted to alter a size of the cut-out formed in the inner tube to thereby move the inner tube relative to the outer tube. In another embodiment, the locking mechanism can be movable between a first position, in which the locking mechanism extends longitudinally relative to a longitudinal axis of the outer tube, and a second position in which the locking mechanism extends transversely outward relative to a longitudinal axis of the outer tube. The locking mechanism can be, for example, an arm pivotally coupled to the outer tube and a linkage pivotally coupled between the arm and the inner tube.

In use, pivotal movement of the locking mechanism can be adapted to pull the linkage proximally to move the inner tube proximally relative to the outer tube. In an exemplary embodiment, the locking mechanism is coupled to a proximal end of the outer tube.

In yet another embodiment, a surgical method is provided and includes positioning a head of a bone anchor between a distal end of an outer tube and a distal end of an inner tube disposed within the outer tube, and pivoting a locking mechanism pivotally coupled to a proximal portion of the outer tube to move the locking mechanism from an unlocked position to a locked position and thereby slide the inner tube relative to the outer tube to engage the head of the bone anchor between the distal ends of the inner and outer tubes. The method can also include implanting the bone anchor in bone, positioning a spinal fixation element within the head of the bone anchor, inserting a fastening element through the extension device, and mating the fastening element to the head of the bone anchor to lock the spinal fixation element within the head of the bone anchor. The method can further include moving the locking mechanism from the locked position to the unlocked position to release the head of the bone anchor from the distal ends of the inner and outer tubes. The locking mechanism can include, for example, a cam that moves the inner tube relative to the outer tube, or a hinge that moves the inner tube relative to the outer tube.

BRIEF DESCRIPTION OF THE DRAWINGS

The invention will be more fully understood from the following detailed description taken in conjunction with the accompanying drawings, in which:

FIG. 1A is a perspective view of one embodiment of a bone anchor extension having opposed pivoting arms for engaging a bore anchor, and a sliding locking mechanism shown in the locked position for preventing pivotal movement of the opposed arms;

FIG. 1E is a side view of the bone anchor extension of FIG. 1A, showing tangs for maintaining the locking mechanism in a fixed position;

FIG. 1F is a cross-sectional view of the bone anchor extension of FIG. 1E;

FIG. 2A is a perspective view of another embodiment of a bone anchor extension having opposed pivoting arms for engaging a bone anchor, and a sliding locking mechanism shown in the locked position for preventing pivotal movement of the opposed arms;

FIG. 5B is a side view of the bone anchor extension of FIG. 5A in the assembled configuration, showing the hinged locking mechanism in an unlocked position;

FIG. 5C is a side view of the bone anchor extension of FIG. 5A in the assembled configuration, showing the hinged locking mechanism in a locked position;

FIG. 5D is a cross-sectional view of the bone anchor extension of FIG. 5B, taken along a longitudinal axis of the device;

FIG. 5E is a cross-sectional view of the bone anchor extension of FIG. 5C, taken along a longitudinal axis of the device;

FIG. 6D is a cross-sectional view of the bone anchor extension of FIG. 6B, taken along a longitudinal axis of the device;

FIG. 6E is a cross-sectional view of the bone anchor extension of FIG. 6C, taken along a longitudinal axis of the device;

DETAILED DESCRIPTION OF THE INVENTION

Figure 1B:
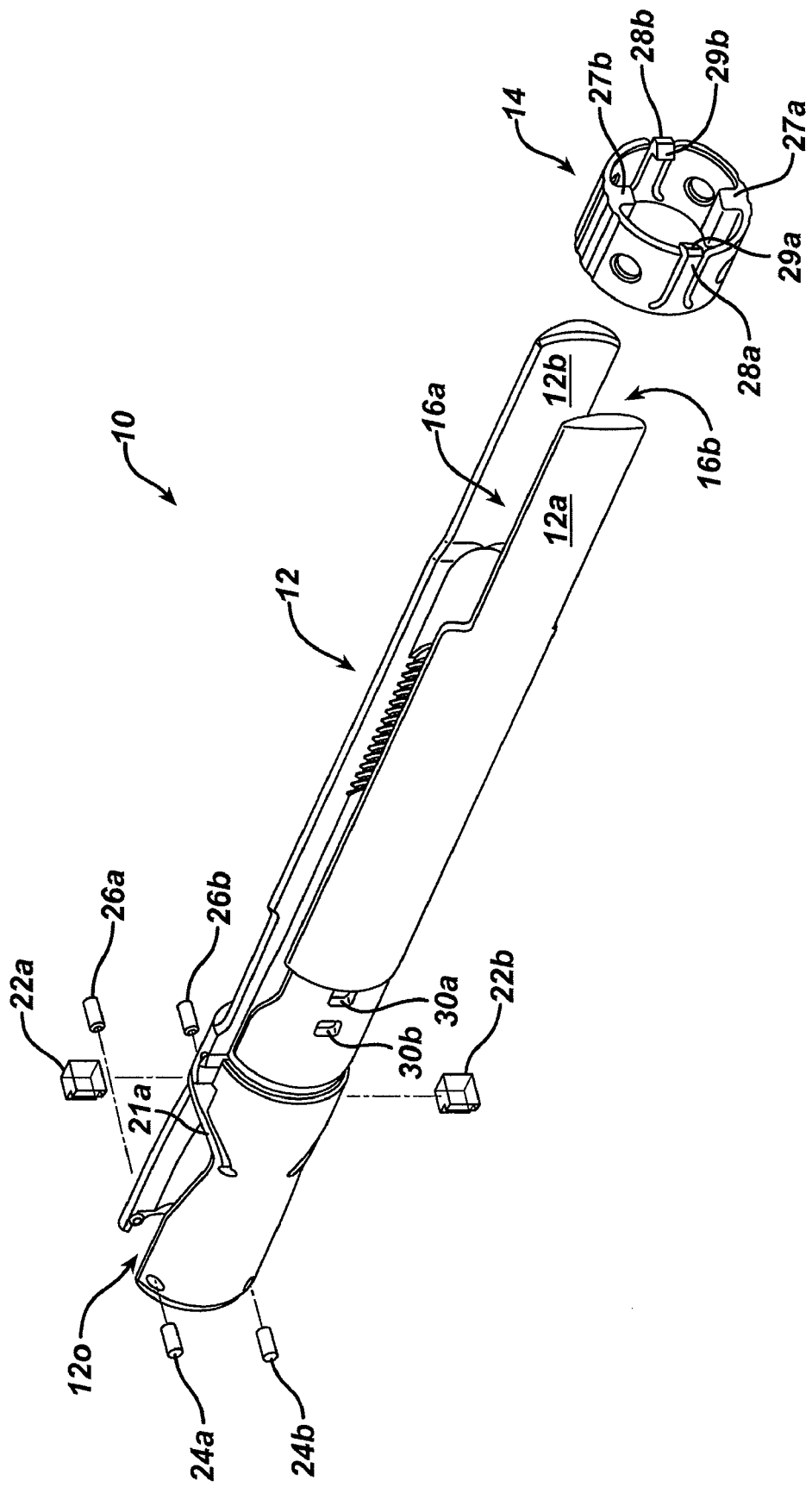
FIG. 1B is an exploded view of the bone anchor extension of FIG. 1A.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for facilitating delivery and implanting of a bone anchor, such as a bone screw, into bone, such as one or more vertebral bodies of the spine. In one exemplary embodiment, a bone anchor extension is provided for coupling to a bone anchor to facilitate delivery and implanting of the bone anchor in bone. The bone anchor extension can have a generally elongate configuration that allows it to extend from a skin incision in a patient to a site proximate a patient's spine, and it can include a lumen extending therethrough between proximal and distal ends thereof. A distal end of the bone anchor extension can be adapted to engage a bone anchor, such as a bone screw. Various techniques are provided for locking the distal end of the bone anchor extension into engagement with a bone anchor. In use, the bone anchor extension provides a percutaneous pathway between a skin incision and a bone anchor mated to the distal end of the bone anchor extension, thereby allowing components of the bone anchor, such as a fastening mechanism, a spinal fixation element, and/or other instruments to be delivered in a minimally invasive manner to the bone anchor and surrounding surgical site. Although the methods and devices disclosed herein are designed primarily for use in spinal applications, one skilled in the art will appreciate that the methods and devices can be used to facilitate the implantation of any type of bone anchor to any type of bone.

FIGS. 1A-1F illustrate one exemplary embodiment of a bone anchor extension for use in delivering and implanting bone anchors in bone, such as one or more vertebral bodies of the spine. The bone anchor extension generally includes a hollow elongate member 12 having an inner lumen 12o extending therethrough and adapted to span from at least a skin incision in a patient to a predetermined site proximate a spine of the patient. The hollow elongate member 12 has opposed arms 12a, 12b that are coupled by at least one fulcrum such that the opposed arms 12a, 12b are adapted to pivot relative to one another, i.e., to move toward and away from one another, to releasably engage a bone anchor between a distal end 12d of the opposed arms 12a, 12b. The bone anchor extension 10 also includes a locking mechanism 14 disposed between the opposed arms 12a, 12b and movable between an unlocked position in which the opposed arms 12a, 12b are free to pivot relative to one another, and a locked position in which the locking mechanism 14 prevents pivotal movement of the opposed arms 12a, 12b to lock a bone anchor into engagement with the opposed arms 12a, 12b.

The elongate member 12 can have a variety of configurations. In the illustrated embodiment, the elongate member 12 has a generally cylindrical shape with an inner lumen 12o extending therethrough between proximal and distal ends 12a, 12b thereof. Opposed slots 16a, 16b are formed in the hollow elongate member 12 and they extend along various portions of the length of the elongate member 12 to separate the elongate member 12 into two halves, each of which forms an arm 12a, 12b. The opposed arms 12a, 12b are configured to engage a bone anchor, such as a bone screw, between the distal ends 12d thereof. While various techniques can be used to allow the arms 12a, 12b to engage a bone anchor, in an exemplary embodiment the arms 12a, 12b are pivotally coupled to one another such that the distal ends 12d of the arms 12a, 12b can pivot between open and closed positions. As shown in FIGS. 1A-1F, the opposed arms 12a, 12b are connected to one another at a pivot point $P_1$ that is located adjacent to, but proximal of the distal end 12d of the elongate member 12. The pivot point $P_1$ includes a hinge extending across the opposed slots 16a, 16b and between the opposed arms 12a, 12b, and a fulcrum positioned between each arm 12a, 12b. The hinge can be defined by the shape of the slots 16a, 16b formed in the elongate member 12. In the illustrated embodiment slots 16a, 16b do not extend through the pivot point $P_1$, leaving a portion that connects the arms 12a, 12b. In particular, as best shown in FIGS. 1E-1F, the distal portion of the slots 16a, 16b each include an enlarged, curved terminal end 17a, 17b located adjacent to the pivot point $P_1$. A second curved slot 20a, 20b can also be formed adjacent to the curved terminal end 17a, 17b of the distal portion of each slot 16a, 16b to define a curved spring 21a, 21b that extends between the arms 12a, 12b. The curved spring 21a, 21b will allow the arms 12a, 12b to extend away from and toward one another, thereby allowing pivotal movement of the arms 12a, 12b. As indicated above, the pivot point $P_1$ can also include a fulcrum disposed between the arms 12a, 12b such that the arms 12a, 12b will pivot about the fulcrum. In the illustrated embodiment, the fulcrum is in the form of first and second blocks 22a, 22b (FIG. 1B) that are positioned between the arms 12a, 12b just proximal to the springs 21a, 21b. In use, movement of the proximal portion of each arm 12a, 12b toward one another will cause the distal portion of each arm 12a, 12b to move away from one another, and vice versa, thereby allowing a bone anchor to be engaged between the distal ends 12d of the arms 12a, 12b.

In order to facilitate engagement of a bone anchor between the distal ends 12d of the arms 12a, 12b, the arms 12a, 12b can include an engagement mechanism formed thereon. While various engagement mechanisms can be used, in one exemplary embodiment each arm 12a, 12b can include a lip 18a, 18b formed on an inner surface thereof and adapted to be received within and to engage a corresponding groove formed in a bone anchor, such as a bone screw. In use, the distal portion of the arms 12a, 12b can pivot away from one another to allow the arms 12a, 12b to be positioned around the bone anchor, and they can pivot toward one another to allow the lips 18a, 18b to extend into and engage the corresponding grooves in the bone anchor, thereby mating the bone anchor extension 10 to the bone anchor. The arms 12a, 12b can also include various other features, such as an anti-rotation mechanism formed on a distal end 12d of the opposed arms 12a, 12b for preventing rotation of a bone anchor engaged between the opposed arms 12a, 12b. In one embodiment as shown in FIGS. 1A and 1B, the anti-rotation mechanism can be in the form of first and second pins 24a, 24b extending inward from opposed outer regions of the first arm 12a, and first and second pins 26a, 26b extending inward from opposed outer regions of the second arm 12b. The pins can be positioned to extend into opposed slots formed in a bone anchor, thus engaging the bone anchor therebetween to prevent rotation of the bone anchor relative to the bone anchor extension 10. A person skilled in the art will appreciate that a variety of other techniques can be used to mate the bone anchor extension 10 to a bone anchor, and that the particular configuration of the engagement mechanism can vary depending on the configuration of the bone anchor.

Figure 1C:
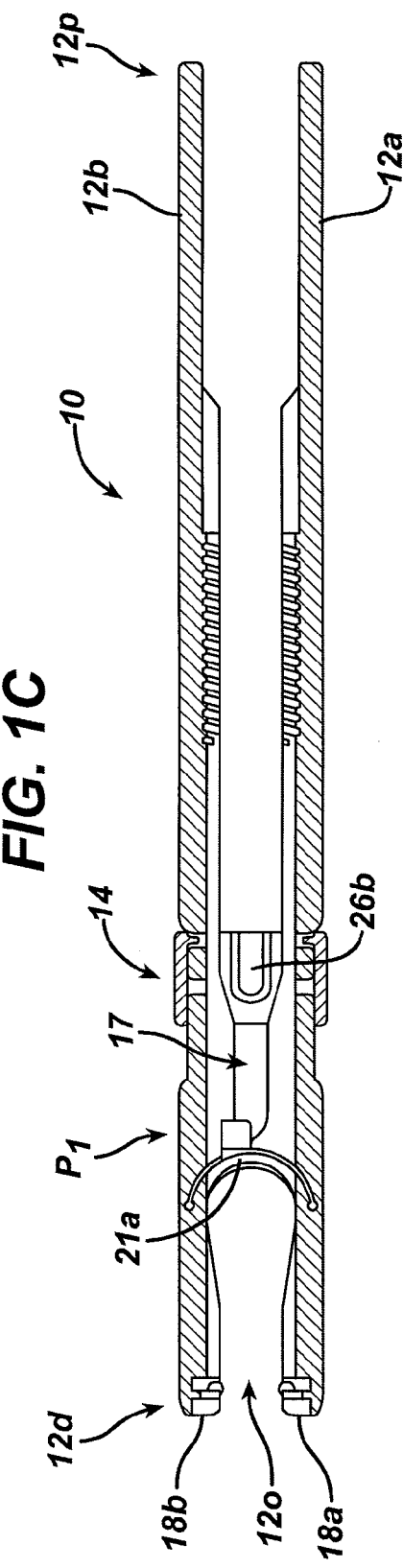
FIG. 1C is a cross-sectional view of the bone anchor extension of FIG. 1A, showing the locking mechanism in an unlocked position.
Figure 1D:
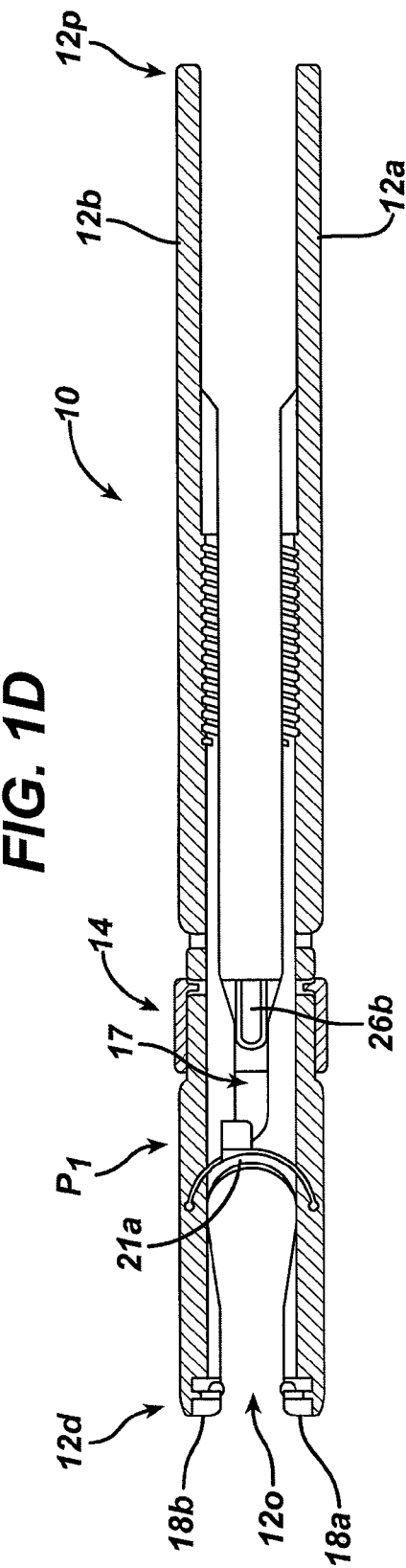
FIG. 1D is a cross-sectional view of the bone anchor extension of FIG. 1A, showing the locking mechanism in a locked position.

As previously indicated, the bone anchor extension 10 can also include a locking mechanism that is adapted to lock a bone anchor into engagement with the bone anchor extension 10, thereby preventing inadvertent disengagement of the bone anchor extension 10 from the bone anchor during use of the device. In the embodiment shown in FIGS. 1A-1F, the locking mechanism is in the form of a single or unitary locking band 14 that is adapted to slidably move along the elongate member 12 between an unlocked position in which the locking band 14 allows free pivotal movement of the opposed arms 12a, 12b relative to one another, and a locked position in which the locking band 14 prevents pivotal movement of the opposed arms 12a, 12b relative to one another to lock a bone anchor into engagement with the distal ends 12d of the arms 12a, 12b. As best shown in FIG. 1B, the locking band 14 has a generally annular shape and includes opposed protrusions or blocks 27a, 27b formed on an inner surface thereof. Each block 27a, 27b is shaped to extend between the opposed slots 16a, 16b formed in the elongate member 12. In order for the blocks 27a, 27b to allow free pivotal movement of the arms 12a, 12b when the blocks 27a, 27b are located in an unlocked position and to prevent pivotal movement of the arms 12a, 12b when the blocks 27a, 27b are located in a locked position, a width between the opposed slots 16a, 16b formed in the elongate member 12 can vary. In particular, as shown in FIGS. 1C and 1D, the proximal portion of the slots 16a, 16b can decrease in width just proximal of and adjacent to the pivot point $P_1$ to form a narrowed region 17. The blocks 27a, 27b can have a width that is substantially the same as the width of the narrowed region 17. As a result, when the blocks 27a, 27b on the locking band 14 are located proximal of the narrowed region 17, i.e., when the locking band 14 is in a proximal position, the arms 12a, 12b can pivot freely to allow the distal ends 12d of the arms 12a, 12b to be positioned around a bone anchor. FIG. 1C illustrates the locking band 14 in the proximal unlocked position with the block 27b positioned proximal of the narrowed region 17. When the locking band 14 is slid distally along the elongate member 12, the blocks 27a, 27b can extend into the narrowed region 12 and between the opposed arms 12a, 12b. The blocks 27a, 27b will thus prevent pivotal movement of the opposed arms 12a, 12b about the blocks 22a, 22b that form the fulcrum, thereby locking the arms 12a, 12b in a fixed position. Since the distal portion of the arms 12a, 12b cannot move away from one another, a bone anchor engaged between the distal ends 12d of the arms 12a, 12b will be locked therebetween. The distal portion of the arms 12a, 12b are also prevented from moving toward one another as well due to the configuration of the locking band 14. FIG. 1D illustrates the locking band 14 in the distal locked position with the block 27b is positioned within the narrowed region 17 to prevent pivotal movement of the arms 12a, 12b.

In order to maintain the locking band 14 in the proximal unlocked position and the distal locked position, the locking band 14 can also include an engagement mechanism formed thereon for releasably engaging the elongate member 12. As shown in FIG. 1B, the locking band 14 includes opposed deflectable tangs 28a, 28b formed thereon. The tangs 28a, 28b, for example, can be formed by cut-outs in the locking band 14. Each tang 28a, 28b can include a protrusion 29a, 29b formed on a distal end thereof and adapted to extend into a corresponding detent or opening formed in the elongate member 12. FIG. 1B illustrates proximal and distal openings 30a, 30b formed in arm 12a. While not shown, the other arm 12b can likewise include proximal and distal openings formed therein. When the locking band 14 is in the proximal unlocked position, the protrusion 29a, 29b on each tang 28a, 28b can extend into the proximal opening in each arm 12a, 12b, thereby engaging the elongate member 12 and thus maintaining the locking band 14 in the proximal unlocked position. When a force is applied to the locking band 14 to slide the locking band 14 distally, the arms 12a, 12b will deflect outward to remove the protrusions 29a, 29b from the openings. When the locking band 14 is in the distal position, i.e., when the blocks 27a, 27b are located within the narrowed region 17 of the slots 16a, 16b, the protrusions 29a, 29b on the tangs 28a, 28b will extend into and engage the distal openings in the arms 12a, 12b to maintain the locking band 14 in the distal locked position. FIGS. 1E and 1F illustrate the locking band 14 in the distal locked position, showing protrusion 29a extending into the distal opening 30b formed in arm 12a. Again, a force can be applied to the locking band 14 to cause the arms 12a, 12b to deflect outward and thereby allow the locking band 14 to be slid proximally to return to the proximal unlocked position.

Figure 2B:
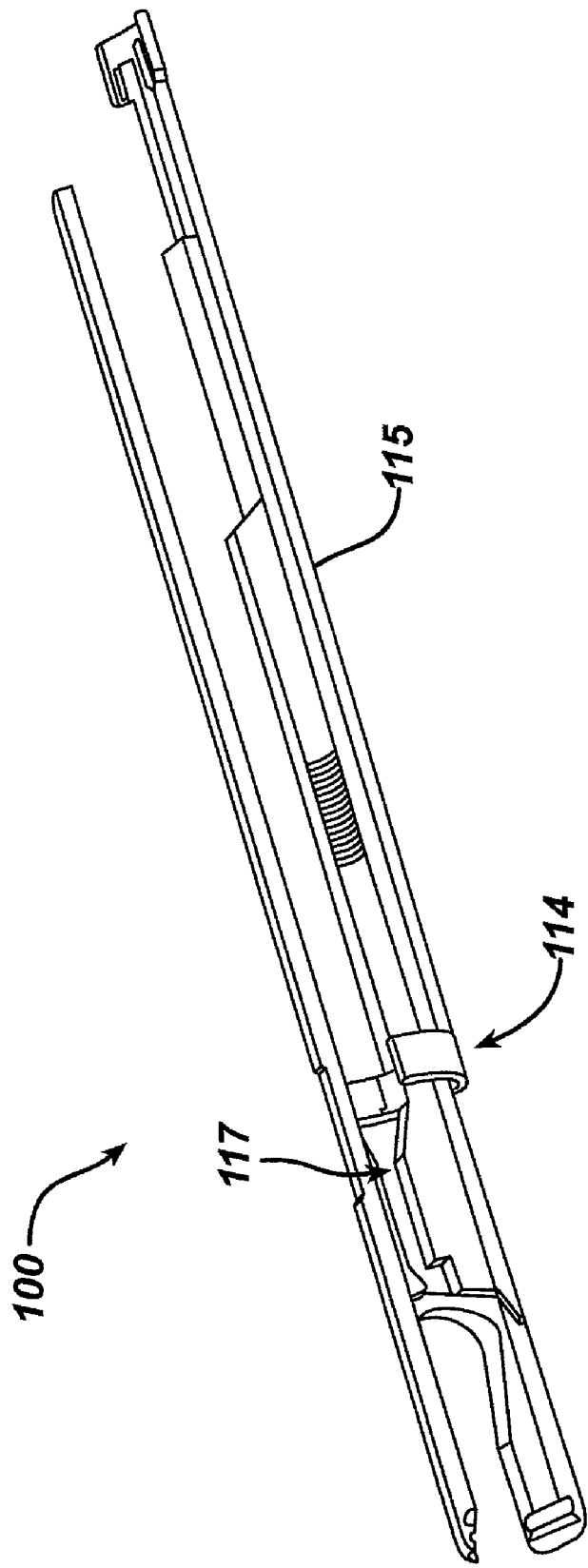
FIG. 2B is a cross-sectional view of the bone anchor extension of FIG. 2A, with the locking mechanism in the unlocked position.
Figure 2C:
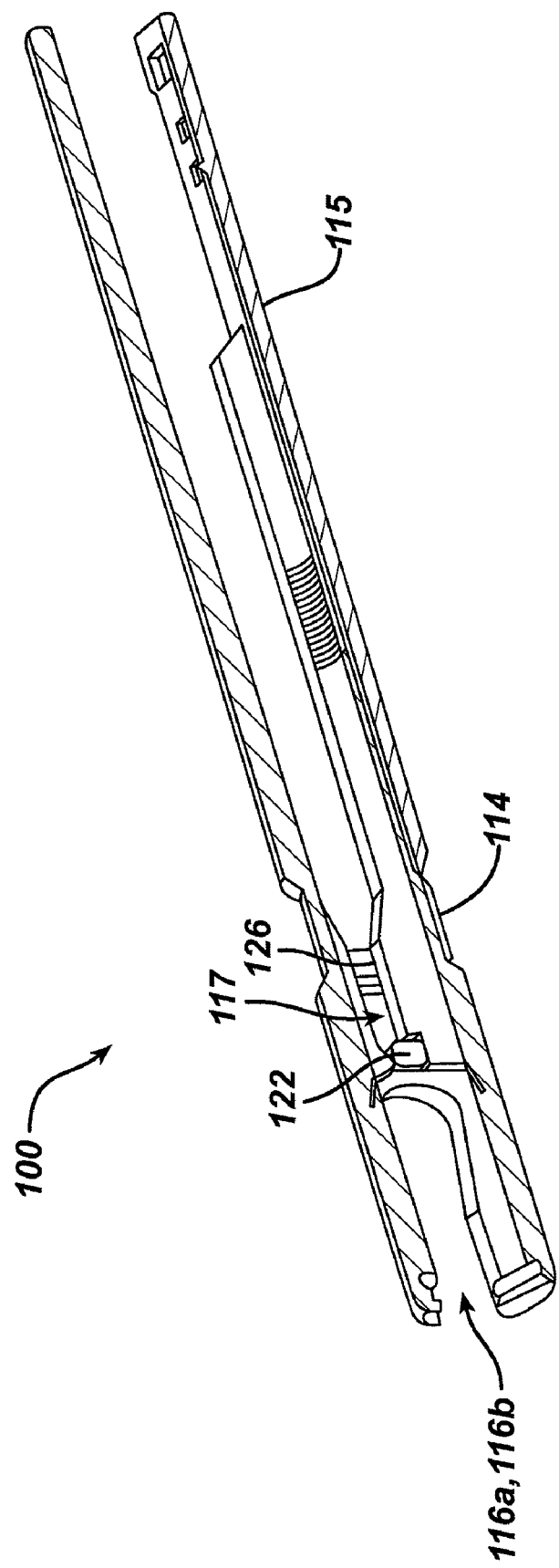
FIG. 2C is a cross-sectional view of the bone anchor extension of FIG. 2A, with the locking mechanism in the locked position.

In use, since the bone anchor extension is preferably inserted through a skin incision and extends to an anchor site, only a proximal portion of the bone anchor extension will extend outside of the patient's body. Thus, an actuator, such as a driver tool, grasper, or other device, can be inserted through or along side the elongate member, and it can be used to engage the locking band to slide it between the proximal and distal positions. Alternatively, the actuator can be formed on the locking band. For example, the locking band can include an extension arm or handle formed thereon and configured to be grasped by a user at the proximal end of the device. FIGS. 2A-2C illustrate one exemplary embodiment of a bone anchor extension 100 having a locking band 114 that is similar to the locking band 14 shown in FIGS. 1A-1F, but that includes an elongate extension arm 115 formed thereon. In particular, the arm 115 is mated to or integrally formed on a portion of the locking band 114, and it extends in a proximal direction along an outer surface of one of the arms 112a, 112b of the elongate member 112. A proximal end 115p of the extension arm 115 can extend proximally beyond a proximal end 112p of the elongate member 112, thus allowing a user to grasp the proximal end 115p of the extension arm 115. The user can thus move the arm 115 proximally and distally, thereby sliding the locking band 114 between the unlocked and locked positions.

FIGS. 2A-2C also illustrate an alternative embodiment of a locking band 114. In this embodiment, the locking band 114 is not annular, but rather is substantially C-shaped such that it extends around only a portion of the elongate member 112. The locking band 114 still functions similar to the locking band 14 shown in FIGS. 1A-1F. In particular, locking band 114 includes a block 126 formed on an inner surface thereof as shown in FIG. 2C. When the locking band 114 is in the proximal position, as shown in FIGS. 2A and 2B, the block will be positioned proximal of the narrowed region 117 of the opposed slots 116a, 116b, thus allowing free pivotal movement of the opposed arm 112a, 112b. When the locking band 114 is moved distally into the distal locked position, as shown in FIG. 2C, the block 126 will be positioned within the narrowed region 117 and just proximal of the block 122 that forms the fulcrum, thus preventing pivotal movement of the opposed arms 112a, 112b and locking a bone anchor between the distal ends of the arms 112a, 112b.

Figure 3A:
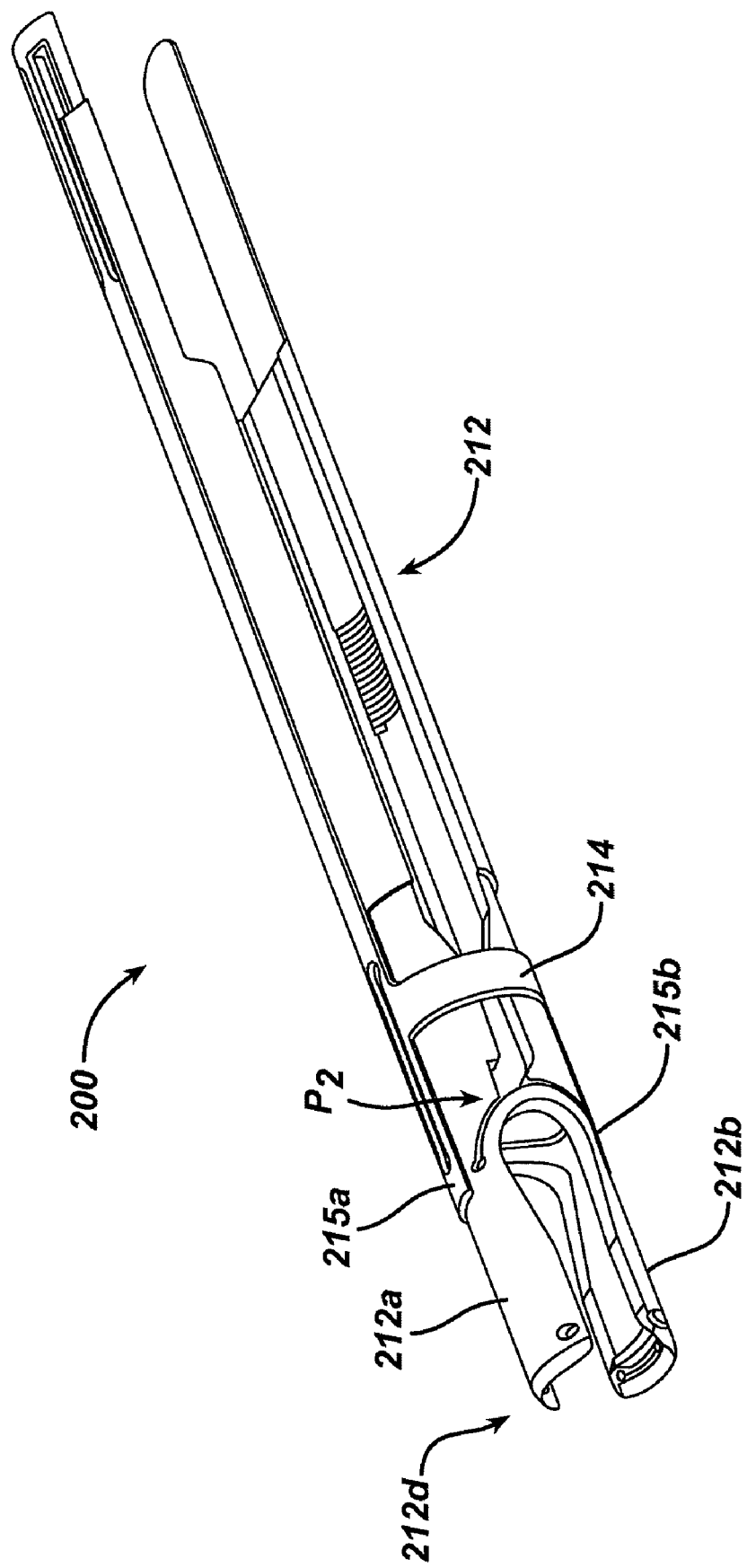
FIG. 3A is a perspective view of yet another embodiment of a bone anchor extension having opposed pivoting arms for engaging a bone anchor, and a sliding locking mechanism shown in the locked position for preventing pivotal movement of the opposed arms.
Figure 3B:
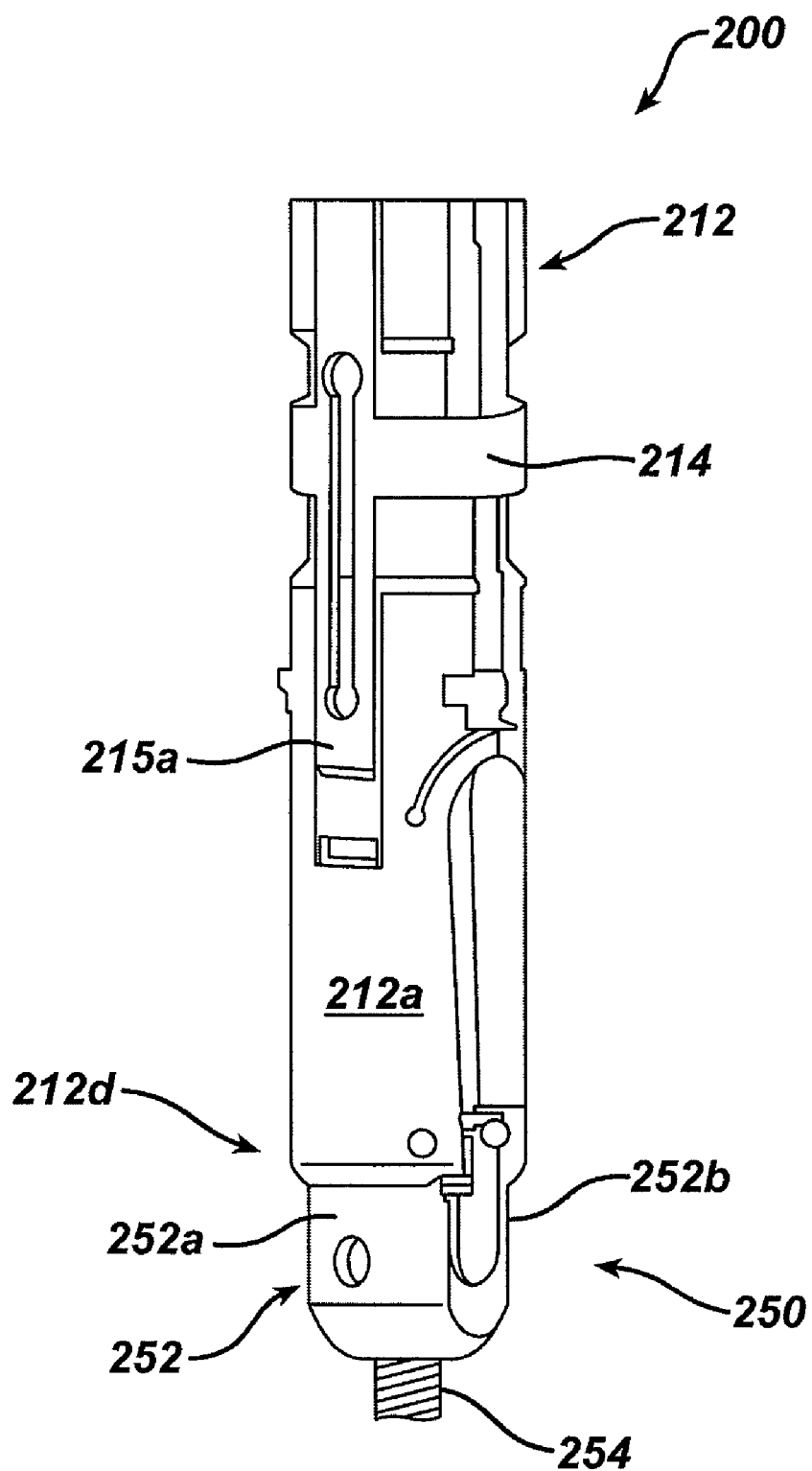
FIG. 3B is a side view of a distal portion of the device of FIG. 3A, showing a bone anchor coupled to a distal end of the device in the unlocked position.

The locking band can also include features to further prevent disengagement between a bone anchor and the distal ends of the opposed arms of the elongate member. FIGS. 3A-3B illustrate another embodiment of a bone anchor extension 200 having a locking band 214 that is similar to the locking bands 14, 114 shown in the previous embodiments, but that includes opposed extension arms 215a, 215b extending distally from the band 214. When the locking band 214 is in the proximal unlocked position, as shown in FIG. 3A, the extension arms 215a, 215b will be positioned adjacent to or proximal of the pivot point $P_2$ so as to not interfere with pivotal movement of the arms 212a, 212b of the elongate member 212. When the locking band 214 is moved to the distal position the extension arms 215a, 215b will be positioned adjacent to a distal portion of the opposed arms 212a, 212b of the elongate member 212. As a result, the extension arms 215a, 215b will help prevent outward deflection of the distal end 212d of the opposed arms 212a, 212b of the elongate member 212, thereby further preventing disengagement between a bone anchor and the bone anchor extension 200.

FIG. 3B also illustrates an exemplary bone anchor 250 that is matable to a distal end of the bone anchor extensions of FIGS. 1A-4B. By way of non-limiting example, the bone anchor 250 is shown coupled to the bone anchor extension 200 of FIG. 3B. One skilled in the art will appreciate, however, that the bone anchor extensions disclosed herein are not limited to use with the illustrated bone anchor 250 but instead may be configured for use with any type of bone anchor, e.g., bone screw or hook; mono-axial or polyaxial.

In general, the bone anchor 250 includes a receiving member or head 252 that is configured to receive and couple a spinal fixation element, such as a spinal rod or spinal plate, to bone, and a distal bone engaging portion 254, such as an externally threaded screw shank. The head 252 of the bone screw 250 has a generally U-shaped configuration with opposed arms 252a, 252b and opposed U-shaped slots formed between the arms 252a, 252b. The slots are configured to receive a spinal fixation element, such as a spinal rod. In order to mate the bone screw 250 to the distal end 212d of the bone anchor extension 200, the proximal end of the head 252 can include at least one groove formed radially around at least a portion of an outer surface of each arm 252a, 252b of the head 252. Each groove is adapted to receive a corresponding lip formed on an inner surface of the distal end 212d of each arm 212a, 212b of the bone anchor extension 200. The lips can be positioned within the grooves by squeezing a proximal end of the arms 212a, 212b toward one another to open or expand the distal portion of the arms 212a, 212b. The arms 212a, 212b can then be released to allow the distal ends 212d to come together and engage the head 252. Once mated, the locking band 214 can be moved to the locked position to lock the bone anchor 250 into engagement with the bone anchor extension 200, thereby preventing separation of the bone anchor extension 200 and bone anchor 250 until desired.

Figure 4A:
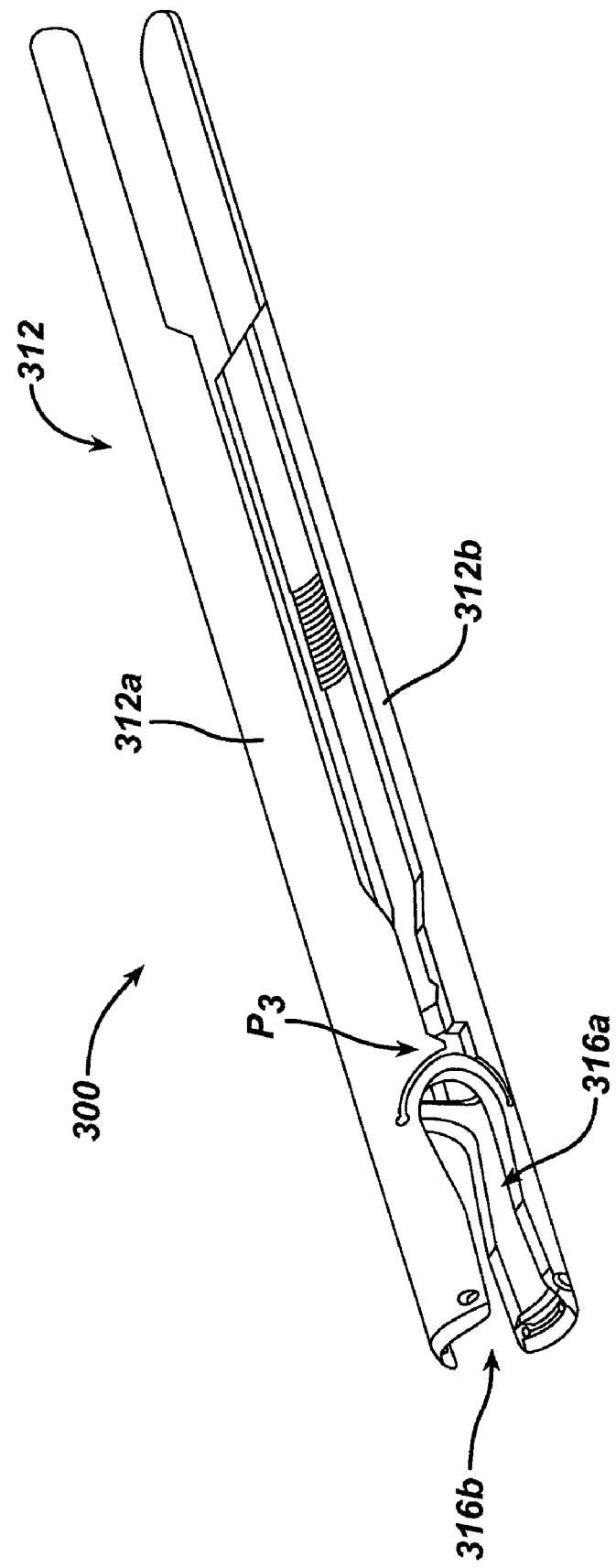
FIG. 4A is a perspective view of another embodiment of a bone anchor extension having opposed pivoting arms for engaging a bone anchor.
Figure 4B:
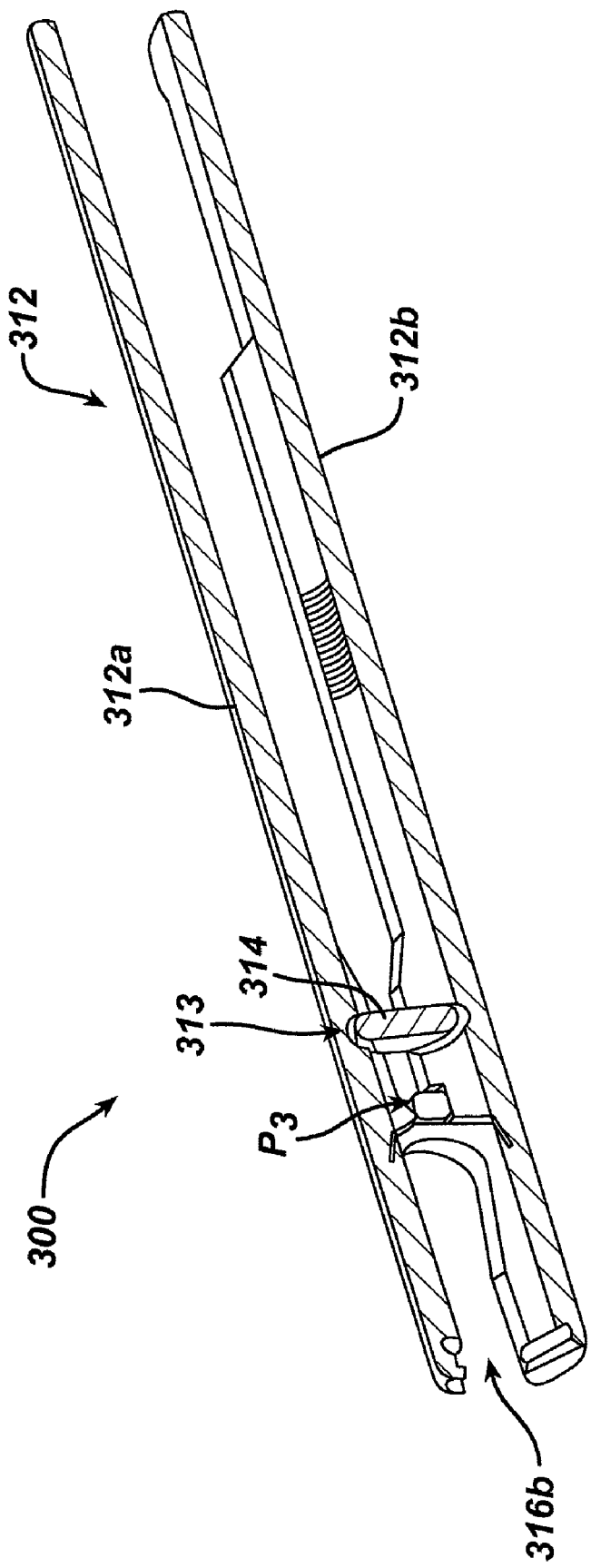
FIG. 4B is a cross-sectional view of the bone anchor extension of FIG. 4A, showing a rotating locking mechanism shown in the locked position for preventing pivotal movement of the opposed arms.

A person skilled in the art will appreciate that the locking mechanism can have a variety of other configurations. FIGS. 4A-4B illustrate another embodiment of a bone anchor extension 300 that is similar to the bone anchor extensions described above with respect to FIGS. 1A-3B. In this embodiment, however, the locking mechanism is in the form of a plug 314, rather than a locking band. As shown in FIG. 4B, the plug 314 is rotatably disposed within a cavity 313 formed in the hollow elongate member 312 and located just proximal to the pivot point $P_3$, i.e., proximal to the blocks that formed the fulcrum. The cavity 313 can merely be a cut-out or groove formed on an inner surface of each arm 312a, 312b. The plug 314 can have an asymmetrical shape, such as an oblong or oval shape, such that the plug 314 includes a maximum diameter and a minimum diameter. When the minimum diameter of the plug 314 is aligned with and extends between the opposed arms 312a, 312b, and the maximum diameter of the plug 314 is aligned with and extends between the opposed slots 316a, 316b, the plug 314 will be in the unlocked position to allow pivotal movement of the opposed arms 312a, 312b. The difference between the minimum diameter of the plug 314 and the diameter or width of the cavity 313 formed in the opposed arms 312a, 312b will provide space that allows the arms 312a, 312b to pivot. When the plug 314 is rotated to position the maximum diameter of the plug 314 to extend between the opposed arms 312a, 312b, and the minimum diameter of the plug 314 to extend between the opposed slots 316a, 316b, the plug 314 will be in the locked position to prevent pivotal movement of the opposed arms 312a, 312b. In other words, the maximum diameter of the plug 314 will extend between and be in contact with the cavity 313 formed in the opposed arms 312a, 312b such that the plug 314 does not provide any space to allow the arms 312a, 312b to pivot.

Various techniques can be used to maintain the plug 314 between the opposed arms 312a, 312b. In one embodiment, the cavity 313 in the opposed arms 312a, 312b can have a depth that captures the plug 314 therein, even when the plug 314 is in the unlocked position. In another embodiment, the cavity 313 can include a dovetail configuration that mates with a corresponding dovetail formed on the plug 314, thus allowing the plug 314 to rotate while preventing proximal and distal movement of the plug 314 relative to the elongate member 312. In yet another embodiment, the plug 314 could include a groove formed around a perimeter thereof, and one or both arms 312a, 312b can include a pin extending therethrough and slidably disposed within the groove in the plug 314. The pin(s) will thus allow rotatable movement of the plug 314 while preventing proximal and distal movement of the plug 314 relative to the arms 312a, 312b of the elongate member 31.

Various techniques can also be used to rotate the plug 314 between the locked and unlocked positions. For example, in one embodiment the plug 314 can include an opening or bore extending therethrough. The opening or bore can have an asymmetrical shape, such as a hexagonal shape, that allows a complementary driver mechanism to extend into the opening or bore and thereby engage and rotate the plug 314. In an exemplary embodiment, the opening or bore can have a size that is sufficient to allow a locking mechanism, such as a set screw for locking a spinal fixation element within a bone anchor, to be passed therethrough and delivered to the bone anchor engaged by the distal end of each arm 312a, 312b of the elongate member 312. A person skilled in the art will appreciate that a variety of other techniques can be used to rotate the plug 314 during use of the bone anchor extension.

FIGS. 5A-5E illustrate another embodiment of a bone anchor extension 400 for use in delivering and implanting bone anchors in bone, such as one or more vertebral bodies of the spine. In this embodiment, the bone anchor extension 400 generally includes an inner tube 402 having proximal and distal ends 402p, 402d with a lumen 402c extending therebetween, and an outer tube 404 that is disposed about at least a portion of the inner tube 402. The outer tube 404 can have proximal and distal ends 404p, 404d with a lumen 404c extending therebetween, and it can be sized to span from at least a skin incision in a patient to a predetermined site proximate a spine of the patient. The bone anchor extension 400 can also include a locking mechanism 410 that is coupled to the inner and outer tubes 402, 404 such that movement of the locking mechanism is effective to move the inner tube 402 relative to the outer tube 404 to engage a bone anchor between the distal end 402d of the inner tube 402 and the distal end 404d of the outer tube 404.

The inner and outer tubes 402, 404 can each have a variety of configurations. In the illustrated embodiment, the inner and outer tubes 402, 404 are generally cylindrical and the outer tube 404 is slidably disposed around the inner tube 402 such that the tubes 402, 404 are coaxial. The axial length of the inner and outer tubes 402, 404 can also vary depending on, for example, the patient anatomy, the procedures employed, and/or, the area of the spine in which the device is employed. The inner and outer tubes 402, 404 can also be linear, as in the illustrated embodiment, or they can be curved or angled along one or more sections or the entire length thereof. The inner and outer tubes 402, 404 can be constructed from any suitable biocompatible material, including, for example, a metal, such as stainless steel, or a polymer, from any conventional method of manufacturing medical devices. A person skilled in the art will appreciate that the inner and outer tubes 402, 404 can have various other configurations, including various cross-sectional geometries. Moreover, the tubes 402, 404 need not be coaxial, and the bone anchor extension 400 can include any number of tubes.

Figure 5A:
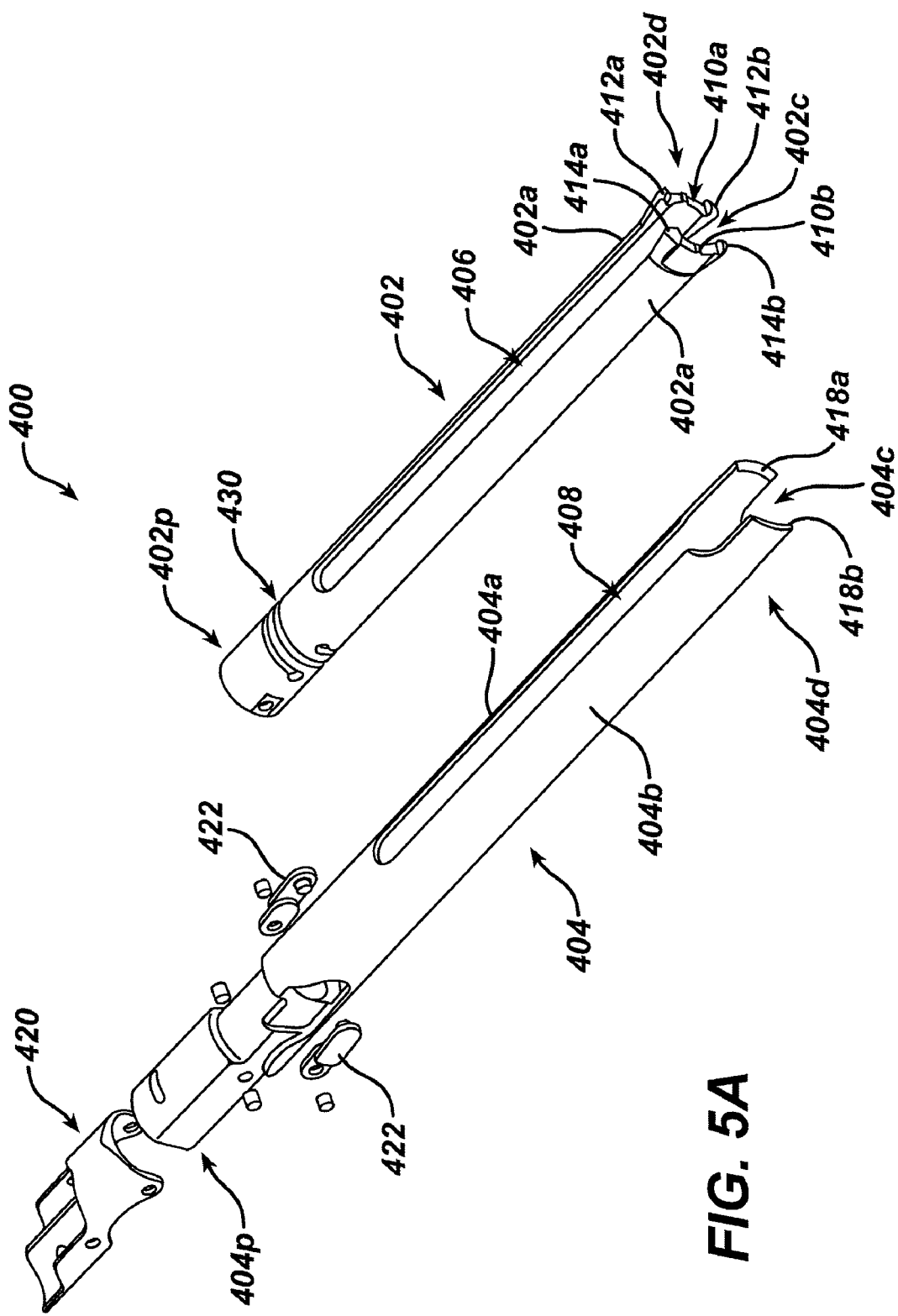
FIG. 5A is an exploded view of another embodiment of a bone anchor extension having opposed arms for engaging a bone anchor, and a hinged locking mechanism shown in a locked position for locking a bone anchor between the opposed arms.

As best shown in FIG. 5A, each tube 402, 404 can also include opposed elongate slots (FIG. 5A illustrates slots 406, 408) formed therein and extending from a distal end 402d, 404d thereof and terminating distal of a proximal end 402p, 404p thereof. The slots 406, 408 define opposed arms 402a, 402b, 404a, 404b of each tube 402, 404, and they can function to allow various tools and devices, such as spinal fixation elements, to be passed therethrough. Prior to locking, the slots 406, 408 can also allow the arms 402a, 402b, 404a, 404b to deflect relative to one another to facilitate engagement of a bone anchor between the distal ends 402d, 404d of the tubes 402, 404. To facilitate positioning of a spinal fixation element, the slots 406, 408 in each tube 402, 404 are preferably aligned with one another along at least a portion of the longitudinal axis of the device 400. The width and length of the slots 406, 408 can vary depending on the particular methods, instruments, and fixation elements being employed. In one exemplary embodiment, for example, the length of the slots 406, 408 is selected to span at least from the skin incision to the distal end 402e, 404d of the inner and outer tubes 402, 404. In such embodiments, the slots 406, 408 can be accessible from outside of the patient. In another exemplary embodiment, the length of the slots 406, 408 is selected to span from the distal end 402a, 402d of the inner and outer tubes 402, 404 to a point distal to the skin incision. In such embodiments, the slots 406, 408 can be accessible only from the lumens of the inner and outer tubes 402, 404. A person skilled in the art will appreciate that the quantity and configuration of the slots can vary, and that the tubes need not include slots.

As previously indicated, the distal end 402d, 404d of the inner and outer tubes 402, 404 can be configured to engage a bone anchor therebetween. While various engagement techniques can be used, in one exemplary embodiment the inner and outer tubes 402, 404 can releasably engage a bone anchor in a manner that allows the bone anchor extension 400 to be connected to the bone anchor during use, e.g., during implantation and/or delivery and/or fastening of a spinal fixation element to the bone anchor, and that allows the bone anchor extension 400 to be disconnected from the bone anchor at the conclusion of the procedure. Preferably, the bone anchor extension can be disconnected remotely, e.g., by manipulation of the proximal end of the bone anchor extension 400, as will be discussed in more detail below.

As shown in FIGS. 5A, 5D, and 5E, in one exemplary embodiment the distal end 404d of the outer tube 404 can include a projection or lip 418a, 418b formed on an inner facing surface of each arm 404a, 404b for engaging corresponding grooves formed in a bone anchor. In use, the arms 404a, 404b can be rotated relative to the bone anchor to slide the lips into the grooves in the bone anchor, as will be described in more detail with respect to FIGS. 7A and 7B. In other embodiments, the arms can flex in the radial direction to facilitate connection to a bone anchor. For example, the arms 404a, 404b can be flexed apart in the radial direction from a first, relaxed position to facilitate advancement of the arms 404a, 404b longitudinally over a portion of the bone anchor. Once positioned about a portion of the bone anchor, the arms 404a, 404b can provide a radially compressive force on the bone anchor as the arms 404a, 404b attempt to return to the first, relaxed position. A person skilled in the art will appreciate that the size, shape, and number of projections formed on each arm 404a, 404b can vary depending on, for example, the opening(s) provided on the bone anchor and the type of connection desired.

As further shown in FIGS. 5A, 5D, and 5E, the distal end 402d of the inner tube 402 can include a contact surface 410a, 410b formed on each arm 402a, 402b that is configured to contact at least a portion of a bone anchor when the inner tube 402 is in the second position, as will be discussed in more detail below. In the illustrated embodiment, the distal end 402d of the inner tube 402 has two opposed generally arcuate contact surfaces 410a, 410b. The contact surfaces 410a, 410b are oriented approximately perpendicular to the longitudinal axis of the inner tube 402 and they are configured to contact a generally arcuate contact surface provided on the proximal end of the bone anchor. In an exemplary embodiment, each contact surface 410a, 410b is complementary in size, shape, and orientation to the contact surface on the bone anchor. One skilled in the art will appreciate that the configuration of each contact surface, e.g., number, size, shape, and orientation of the contact surface, may vary depending on the configuration of the bone anchor.

The distal end 402d of the inner tube 402 and/or the distal end 404d of the outer tube 404 can also optionally include an anti-rotation mechanism configured to inhibit rotation of the bone anchor relative to the bone anchor extension 400. For example, the distal end 402d of the inner tube 402 can include one or more finger-like extensions that extend approximately axially from the distal end 402d of the inner tube 402 and that engage a bone anchor to inhibit rotation of the bone anchor relative to the bone anchor extension. FIG. 5A illustrates opposed extensions 412a, 412b formed on the first arm 402a, and opposed extensions 414a, 414b formed on the second arm 402b. The extension(s) can sit within a groove, recess, slot, or similar structure provided in the bone anchor. Alternatively, the extension(s) can include a contact surface for contacting an axially extending surface of the bone anchor.

As indicated above, the bone anchor extension 400 can also include a locking mechanism for longitudinally adjusting the inner tube 402 relative to the outer tube 404. In an exemplary embodiment, the inner tube 402 is adjustable between a proximal unlocked position in which the distal end 402d of the inner tube 402 is positioned proximal to the distal end 404d of the outer tube 404 as illustrated in FIGS. 5B and 5D, and a distal locked position in which the distal end 402d of the inner tube 402 is positioned proximate to the distal end 404d of the outer tube 404, as shown in FIGS. 5C and 5E. In an exemplary embodiment, the distal end 402d of the inner tube 402 contacts at least a portion of a bone anchor captured by the outer tube 404 when the inner tube 402 is in the distal locked position to engage the bone anchor therebetween. A person skilled in the art will appreciate, however, that various other engagement mechanisms can be used.

While the locking mechanism can have a variety of configurations, in one exemplary embodiment, as shown in FIGS. 5A-5E, the locking mechanism can be in the form of a hinge that is pivotally coupled to the inner and outer tubes 402, 404 such that pivotal movement of the locking mechanism is effective to move the inner tube 402 relative to the outer tube 404 to engage a bone anchor between the distal end 402d of the inner tube 402 and the distal end 404d of the outer tube 404. As shown, the hinge generally includes an arm 420 that is pivotally coupled to the outer tube 404, and a linkage 422 that is pivotally coupled between the arm 420 and the inner tube 402. The arm 420 can have various shapes and sizes. For example, in the illustrated embodiment the arm 420 has a generally elongate configuration and includes a proximal portion 420p that is positioned on one side of the outer tube 404, and a distal portion 420d that is positioned on an opposite side of the outer tube 404. A first pivot point $X_1$ is located between the proximal and distal portions 420p, 420d, and the arm 420 is pivotally attached to the outer tube 404 at the first pivot point $X_1$. As indicated above, the hinge also includes a linkage 422 that is coupled between the arm 420 and the inner tube 402. The linkage 422 can have a variety of configurations, but in the illustrated embodiment the linkage 422 is in the form of an elongate member having proximal and distal ends 422p, 422d. The proximal end 422p of the linkage 422 is pivotally coupled to a terminal end of the distal portion 420d of the arm 420 to form a second pivot point $X_2$ on the hinge, and the distal end 422d of the linkage 422 is pivotally coupled to the inner tube 402 to form a third pivot point $X_3$ on the hinge. In use, when the proximal and distal portions 420p, 420d of the arm 420 are positioned at an angle relative to a longitudinal axis of the outer tube 404, the linkage 422 and the inner tube 402 coupled thereto will be in a proximal unlocked position. As explained above, in the proximal unlocked position the distal end 402d of the inner tube 402 is positioned proximal of the distal end 404d of the outer tube 404, as shown in FIGS. 5B and 5D. When the proximal portion 420p of the arm 420 is moved toward and into longitudinal alignment with the outer tube 404, the distal portion 420d of the arm 420 will likewise move toward and into longitudinal alignment with the outer tube 404. The distal portion 420d of the arm 420 will thus push the linkage 422 into longitudinal alignment with the inner and outer tubes 402, 404, thereby causing the linkage 422 and the inner tube 402 coupled thereto to move distally. Once the arm 420 is in longitudinal alignment with the outer tube 404, the inner tube 402 will be in the distal locked position, as shown in FIGS. 5C and 5E. In this position, a bone anchor can be engaged between the distal ends 402d, 404d of the inner and outer tubes 402, 404. As further shown in FIGS. 5A-5E, the linkage 422 can extend beyond a longitudinal axis of the inner and outer tubes 402, 404 as it is moved from the unlocked position to locked position such that the linkage 422 extends at a slight angle when the arm 420 is in the distal locked position. Such a configuration will help maintain the hinge in the locked position. A person skilled in the art will appreciate that the hinge can have a variety of other configurations.

As further shown in FIG. 5A, the bone anchor extension 400 can also include features to relieve any stress applied to the hinge. For example, a proximal portion of the inner tube 402 can include a relief slit formed thereon and configured to provide relief to the stress applied to the hinge when the hinge is in the locked position. While the relief slit can have a variety of configurations, and it can be located on various portions of the device, in the illustrated embodiment the relief slit is in the form of a spiral cut slit 430 extending radially around a proximal end of the inner tube 402. In use, when the hinge is in the locked position, the inner tube 402 will extend between the hinge and a bone anchor engaged between the distal ends 402d, 404d of the inner and outer tubes 402, 404. The relief slit 430 will compress, decreasing a length of the inner tube 402, to relieve any stress applied to the hinge due to the locking connection between the proximal end 402p of the inner tube 402 and the hinge and the distal end 402d of the inner tube 402 and the bone anchor.

Figure 6A:
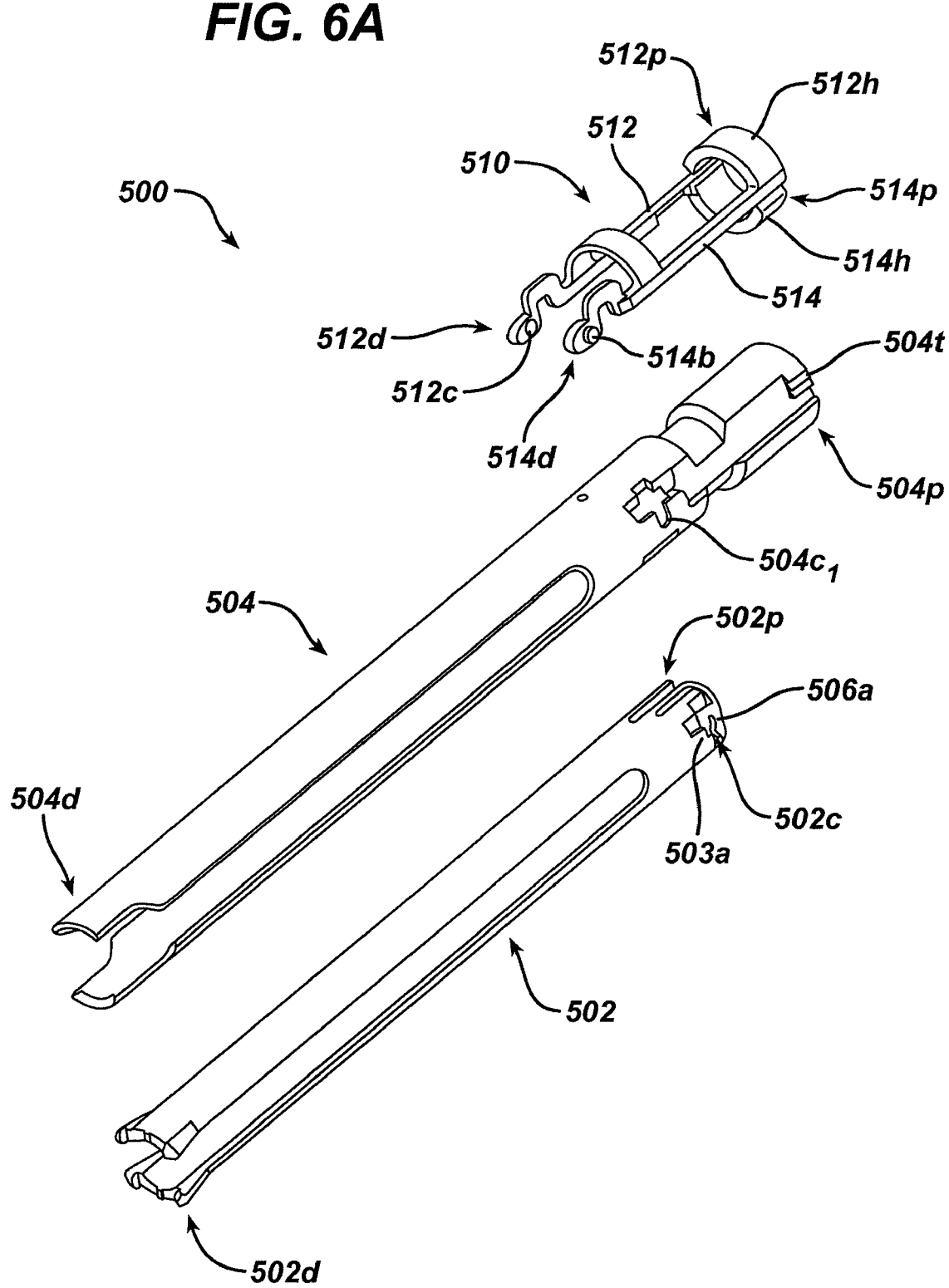
FIG. 6A is an exploded view of another embodiment of a bone anchor extension having opposed arms for engaging a bone anchor, and a cam locking mechanism for locking a bone anchor between the opposed arms.

FIGS. 6A-6E illustrate another embodiment of a bone anchor extension 500 having a locking mechanism for moving an inner tube 502 relative to the outer tube 504 to engage a bone anchor between the distal ends 502d, 504d of the inner and outer tubes 502, 504. In this embodiment, rather than having a hinge that pivots to push and pull the inner tube 502 relative to the outer tube 504, the device 500 includes a locking mechanism 510 that pivots to cam the inner tube 502 proximally and distally relative to the outer tube 504. In general, the locking mechanism 510 includes first and second arms 512, 514 that extend along opposed sides of the outer tube 504, and that each include a proximal end 512p, 514p and a distal end in the form of a cam 512d, 514d. The cam 512d, 514d on each arm 512, 514 can have various shapes and sizes, but is preferably asymmetrical. As shown in FIG. 6A, each cam 512d, 514d is in the form of an oblong or oval shaped member. Each cam 512d, 514d also includes a boss 512b, 514b formed on an outer surface thereof that sits within a cut-out formed in the outer tube 504, and a protrusion (only one protrusion 512c is shown in FIG. 6A) formed thereon that sits within a cut-out formed in the inner tube 502. Each boss and protrusion is configured to pivot relative to the outer and inner tubes 504, 502, respectively, to allow the arms 512, 514 to move between an unlocked position in which the arms 512, 514 extend transversely outward, i.e., at an angle, relative to a longitudinal axis of the outer tube 504, and a locked position in which the arms 512, 514 are longitudinally aligned with a longitudinal axis of the outer tube 504. As each boss and protrusion pivots, the cams 512d, 514d force the inner tube 502 to move relative to the outer tube 504. In particular, when the arms 512, 514 are positioned to extend transversely outward from the outer tube 504, i.e., when the arms 512, 514 are positioned at an angle relative to a longitudinal axis of the outer tube 504 as shown in FIG. 6D, each cam 512d, 514d will be in the first unlocked position. In this position, a minimum diameter of each cam 512d, 514d will extend along the longitudinal axis of the device, and a maximum diameter of each cam 512d, 514d will extend substantially perpendicular to the longitudinal axis of the device. When the arms 512, 514 are pivoted toward the outer tube 504 to longitudinally align the arms 512, 514 with the outer tube 504, as shown in FIG. 6E, the cams 512d, 514d will rotate relative to the inner and outer tubes 502, 504. As the maximum diameter of each cam 512d, 514d approaches alignment with the longitudinal axis, the increasing diameter of each cam 512d, 514d will cause the inner tube 502 to move distally relative to the outer tube 504. In particular, the outer surface of the inner tube 502 includes an abutment (only one abutment 503a is shown in FIGS. 6A, 6D, and 6E) formed on each side thereof and positioned distally adjacent to a cut-out (only one cut-out 502c is shown in FIG. 6A, as will be discussed in more detail below). Each cam 512d, 514d will act against the abutment 503a formed on the inner tube 502 to push the inner tube 502 distally relative to the outer tube 504. As a result, a bone anchor can be engaged between the distal ends 502d, 504d of the inner and outer tubes 502, 504. In order to release the bone anchor, the arms 512, 514 can be moved back to the transverse position, in which the arms 512, 514 extend away from and at an angle relative to a longitudinal axis of the outer tube 504. The cams 512d, 514d will thus return to their original position, allowing the inner tube 502 to move in a proximal direction relative to the outer tube 504.

Figure 6B:
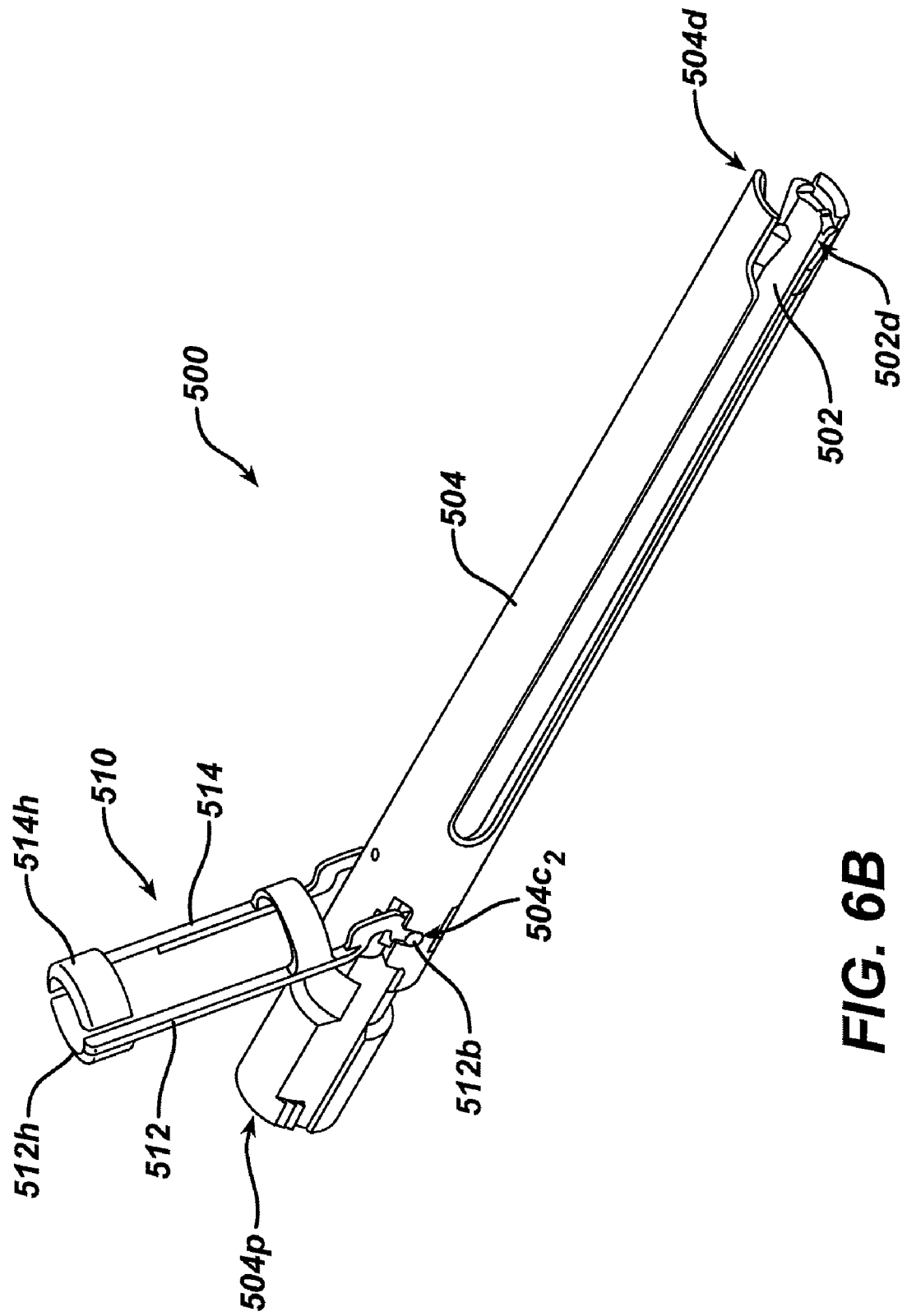
FIG. 6B is a perspective view of the bone anchor extension of FIG. 6A in the assembled configuration, showing the locking mechanism in an unlocked position.

FIG. 6A illustrate an exemplary boss 514b formed on arm 514. As shown, the boss 514b is in the form of a generally circular protrusion or a pin formed on an outer-facing surface of the distal end 514d of arm 514. The boss 514b is configured to extend into a circular or semi-circular cut-out $504c_1$ formed in the outer tube 504. As shown in FIG. 6A, the cut-out $504c_1$ is located a distance distally apart from the proximal end 504p of the outer tube 504. As shown in FIGS. 6B, 6D, and 6E, a second boss 512b is formed on an outer surface of arm 512, and a second cut-out $504c_2$ is formed in an opposed side of the outer tube 504 for rotatably seating the second boss 512b.

FIG. 6A also illustrates an exemplary protrusion 512c formed on an inner-facing surface of the distal end 512d of arm 512. The shape of the protrusion 512c can vary depending on the configuration of the corresponding cut-out formed in the inner tube 502. In an exemplary embodiment, the protrusion 512c is configured to alter a size of the corresponding cut-out formed in the inner tube 502 as the arms 512, 514 are moved between the locked and unlocked positions. This will facilitate movement of the inner tube 50 proximally to the original unlocked position, thus allowing detachment of a bone anchor from engagement between the distal ends 502d, 504d of the inner and outer tubes 502, 504. The protrusion 512c can also act as a mechanical stop to limit rotation of the arms 512, 514 between the unlocked and locked positions. In the embodiment shown in FIG. 6A, the protrusion 512c has a circular portion and a flattened portion formed around a perimeter thereof. FIG. 6A also illustrates a corresponding cut-out 502c formed in the inner tube 502. As shown, the cut-out 502c extends radially around a portion of the proximal end 502p of the inner tube 502 to form a spring arm 506a on the proximal-most end of the inner tube 502. While not shown, a complementary cut-out is formed in an opposed side of the proximal end 502p of the inner tube 502 to form a second spring arm. The spring arm 506a is configured to flex to allow a size of the cut-out 502c to be altered when the protrusion 512c is rotated therein. In particular, the cut-out 502c includes a circular portion that seats the circular portion of the protrusion 512c. When the arms 512, 514 are positioned to extend transversely outward from the outer tube 504, i.e., when the arms 512, 514 are positioned at an angle relative to a longitudinal axis of the outer tube 504 as shown in FIG. 6D, the protrusion 512c will be in the first unlocked position. In this position, the circular portion of the protrusion 512c will rest within the circular portion of the cut-out 502c. The flattened portion of the protrusion 512c will not be in contact with any portion of the corresponding cut-out 502c. When the arms 512, 514 are pivoted toward the outer tube 504 to longitudinally align the arms 512, 514 with the outer tube 504, as shown in FIG. 6E, the protrusion 512c will rotate within the cut-out 502c. The flattened portion of the protrusion 512c will abut against a perimeter of the cut-out 502c, forcing the spring arm 506a proximally away from the remainder of the inner tube 504. The protrusion 512c will thus increase a length of the cut-out 502c, as measured in a proximal-distal direction. This will cause the distal end 502d of the inner tube 502 to move distally toward the distal end 504d of the outer tube 504, further facilitating engagement of a bone anchor between the distal ends 502d, 504d of the inner and outer tubes 502, 504. When the arms 512, 514 are moved back to the transverse position, in which the arms 512, 514 extend away from and at an angle relative to a longitudinal axis of the outer tube 504, the protrusion 512c will return to its original position allowing the spring arm 506a to recoil. The recoil will help pull the inner tube 502 proximally to allow detachment of a bone anchor engaged between the distal ends 502d, 504d of the inner and outer tubes 502, 504. While not shown, a person skilled in the art will appreciate that the distal end 514d of arm 514 can include a protrusion formed on an inner surface thereof, and the inner tube 502 can include a second cut-out formed on an opposed side of the inner tube 502 and defining a second spring arm.

Figure 6C:
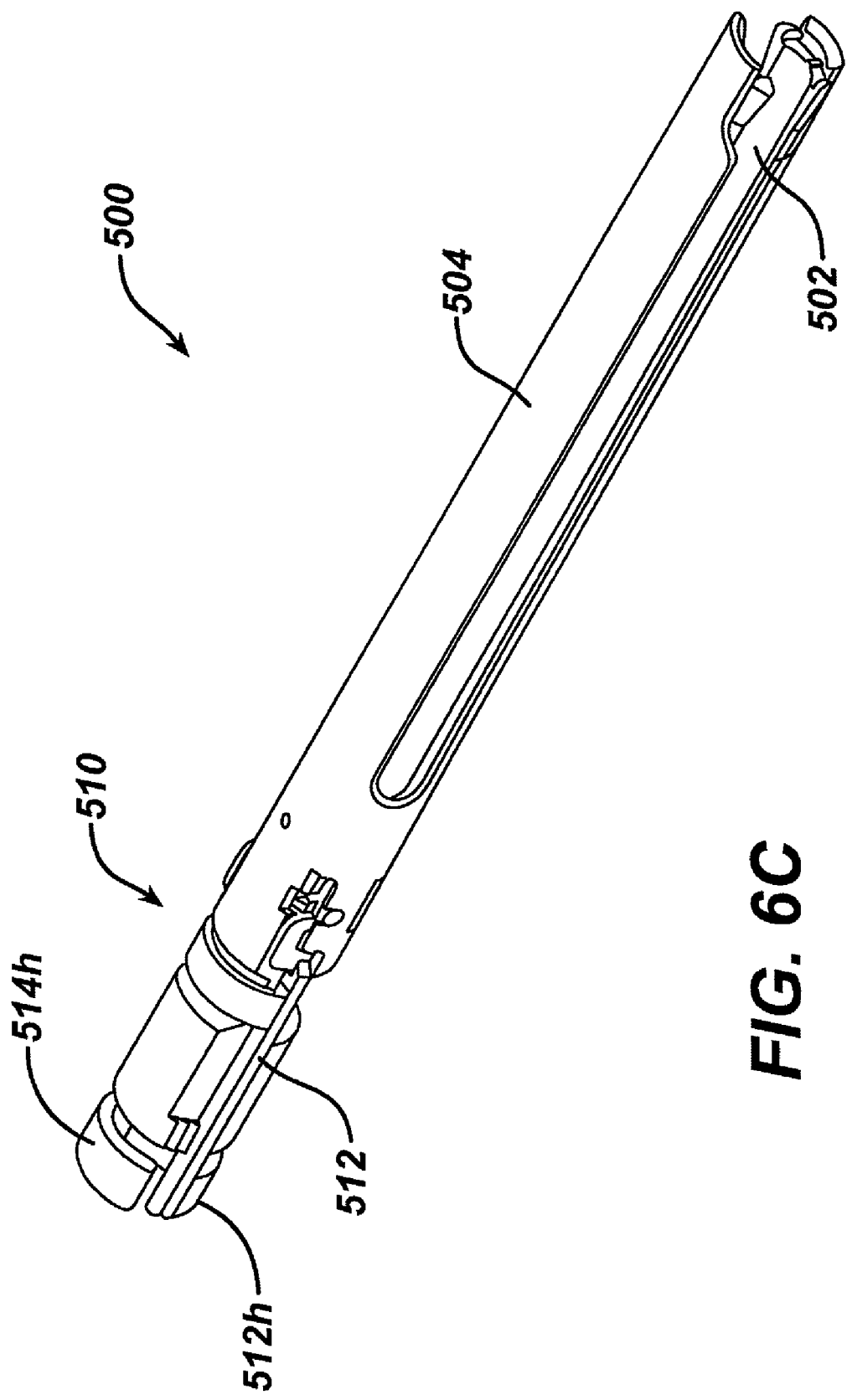
FIG. 6C is a perspective view of the bone anchor extension of FIG. 6A in the assembled configuration, showing the locking mechanism in a locked position.

The locking mechanism 510 can also include a feature that is effective to maintain the locking mechanism 510 in the locked position. While various techniques can be used, in one exemplary embodiment a proximal portion of one or both arms 512, 514 can include one or more teeth formed thereon and configured to engage corresponding teeth formed on the proximal end 504p of the outer tube 504. For example, an inner surface of one of the arms 512, 514 can include teeth (not shown) formed adjacent to but distal of the proximal end 512p, 514p thereof. The outer tube 504 can include corresponding teeth 504t formed thereon, as shown in FIG. 6A, for mating with the teeth on the arm(s) 512, 514 when the arm(s) 512, 514 is in the locked position. One or both arms 512, 514 can also include a handle 512h, 514h formed on a proximal-most end thereof to facilitate grasping of the arms 512, 514, and to release the arms 512, 514 from the locked position. When the arms 512, 514 are in the locked position, the handles 512h, 514h will be positioned proximal to the proximal end 504p of the outer tube 504, as shown in FIG. 6C. In order to release the arms 512, 514 from engagement with the outer tube 504, the handles 512h, 514h can be squeezed together to push the teeth on the arm(s) 512, 514 away from the teeth 504t on the outer tube 504. As a result, the arms 512, 514 can be pivoted away from the outer tube 504 to the unlocked position, shown in FIG. 6B. A person skilled in the art will appreciate that a variety of other techniques can be used to releasably maintain the locking mechanism 510 in a locked position, and that the locking mechanism 510 can have a variety of other configurations.

Figure 7A:
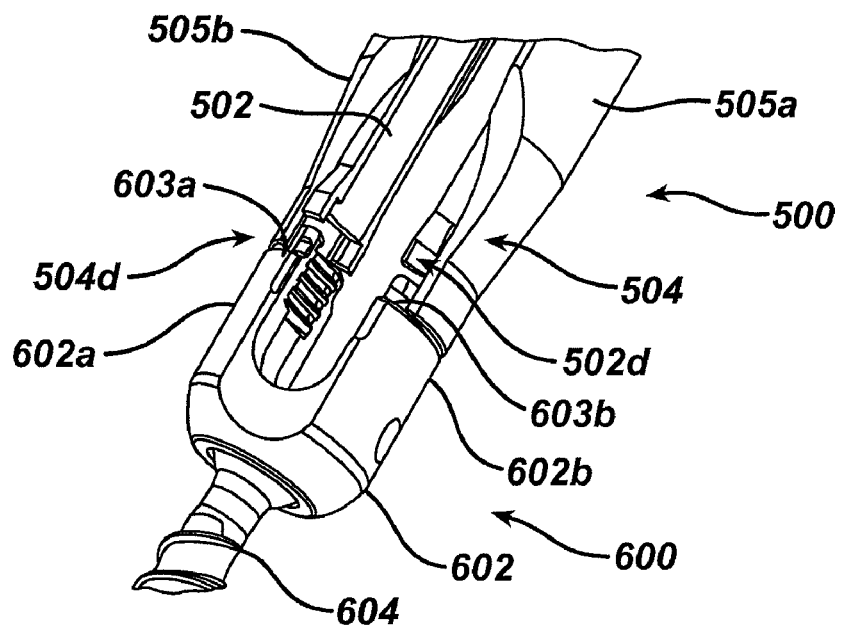
FIG. 7A is a perspective view of a distal portion of a bone anchor extension positioned in relation to a bone anchor, showing the bone anchor extension in the unlocked position.
Figure 7B:
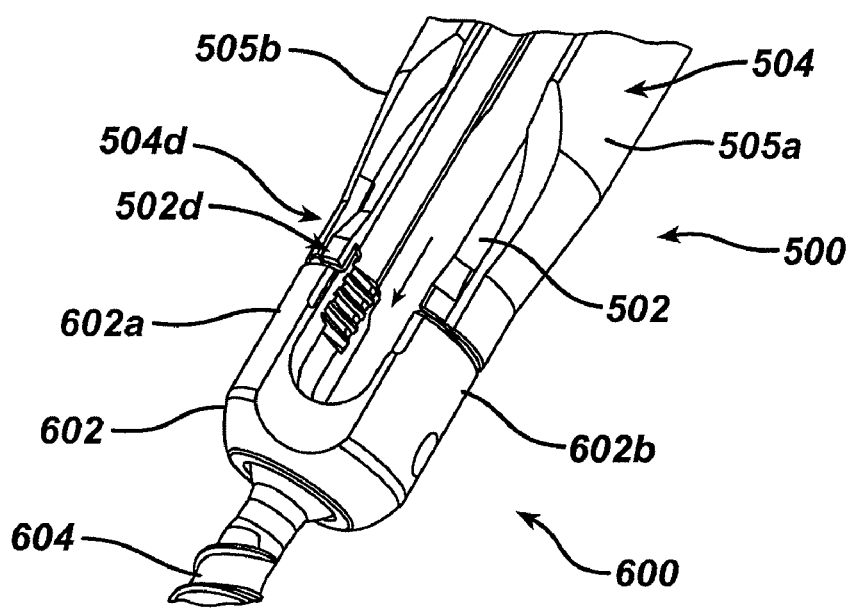
FIG. 7B is a perspective view of the bone anchor extension and bone anchor of FIG. 7A, showing the bone anchor extension in the locked position.

FIGS. 7A and 7B illustrate another exemplary bone anchor 600 that is matable to a distal end of the bone anchor extensions of FIGS. 5A-6E. By way of non-limiting example, the bone anchor 600 is shown coupled to the bone anchor extension 500 of FIGS. 6A-6E, however the bone anchor extensions disclosed herein are not limited to use with the illustrated bone anchor 600 but instead may be configured for use with any type of bone anchor, e.g., bone screw or hook; mono-axial or polyaxial. The bone anchor 600 is similar to the bone anchor 250 previously described with respect to FIG. 3B, and generally includes a bone engaging portion, e.g., a threaded shank 604, and a receiving member or head 602 located on a proximal end of the shank 604. The head 602 includes a groove 603a, 603b formed on an outer surface of each arm 602a, 602b thereof for receiving a corresponding lip formed on an inner surface of a distal end of the outer tube 504. The lips on the outer tube 504 can be positioned within the grooves 603a, 603b on the head 602, as shown in FIG. 7A, by positioning the opposed arms 505a, 505b of the outer tube 504 off-set from the arms 602a, 602b of the head 602 and rotating the bone anchor extension 500 to slide the lips into the grooves 603a 603b. Once mated, the locking mechanism 510 (not shown) can be actuated to move the inner tube 502 to the distal locked position such that the distal end 502d of the inner tube 502 abuts against a proximal-facing surface of each arm 505a, 505b of the head 502. The head 502 will thus be captured between the distal ends 502d, 504d of the inner and outer tubes 502, 504, thereby preventing separation of the bone anchor extension 500 and bone anchor 600 until desired.

In use, the various bone anchor extensions disclosed herein can provide a percutaneous pathway between a skin incision and a bone anchor to facilitate delivery of instruments, spinal fixation elements, and/or components of the bone anchor, such as a closure mechanism, to the bone anchor. In particular, a bone anchor extension can be mated to a bone anchor by actuating the locking mechanism to move it to the locked position, thereby capturing the bone anchor at the distal end of the device. The device, with the bone anchor attached thereto, can be passed through a skin incision to position the bone anchor adjacent to bone. The lumen extending through the bone anchor extension will provide a pathway to the receiving member of the bone anchor. The pathway can allow a driver or other tools to be inserted therethrough for driving the bone anchor into bone, and it can also facilitate delivery of a fastening mechanism, such as a threaded cap or set screw, to the bone anchor. The bone anchor extension can include various features to facilitate delivery of a driver, fastening mechanism, or other instrument or device. For example, the inner lumen of the bone anchor extension can include threads formed therein for mating with corresponding threads formed on a driver mechanism or other instrument or device. The opposed longitudinal slots formed in the bone anchor extension can also be aligned with opposed recesses provided in the receiving member. Alignment of the slots with the recesses can facilitate delivery of a spinal fixation element, such as a spinal rod, to the bone anchor prior to delivering of a fastening mechanism. Methods and devices for spinal fixation element placement are disclosed in commonly owned co-pending U.S. patent application Ser. No. 10/737,537, filed on Dec. 16, 2003, entitled Method and Devices for Spinal Fixation Element Placement and commonly owned co-pending U.S. patent application Ser. No. 10/738,130, filed on Dec. 16, 2003, entitled Method and Devices for Minimally Invasive Spinal Fixation Element Placement, both of which are incorporated herein in by reference in their entireties. Once the bone anchor is implanted, and the procedure is complete, i.e., other components are mated to the bone anchor as may be necessary, the locking mechanism can be returned to the unlocked position, thereby allowing the bone anchor extension to be disengaged from the bone anchor and to be removed from the patient's body.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A bone anchor extension, comprising:
    an inner tube having proximal and distal ends with a lumen extending therebetween;
    an outer tube disposed about at least a portion of the inner tube, the outer tube having proximal and distal ends with a lumen extending therebetween, the outer tube being sized to span from at least a skin incision in a patient to a predetermined site proximate a spine of the patient; and
    a locking mechanism substantially external with respect to the outer tube, the locking mechanism having a proximal portion pivotally coupled to the outer tube and a distal portion pivotally coupled to the inner tube such that pivotal movement of the locking mechanism causes the distal end of the inner tube to move distally toward the distal end of the outer tube to engage a bone anchor therebetween,
    wherein the locking mechanism is movable between a first position, in which the locking mechanism extends longitudinally relative to a longitudinal axis of the outer tube and the proximal portion is positioned on one side of the outer tube and the distal portion is positioned on an opposite side of the outer tube, and a second position in which the locking mechanism extends transversely outward relative to a longitudinal axis of the outer tube.

2. The device of claim 1 wherein the inner and outer tubes are effective to engage and lock a bone anchor between the distal ends thereof when the locking mechanism is in the first position, and wherein a bone anchor can be released from the distal ends of the inner and outer tubes when the locking mechanism is in the second position.

3. The device of claim 1, wherein the locking mechanism comprises an arm pivotally coupled to the outer tube, and a linkage pivotally coupled between the arm and the inner tube such that pivotal movement of the arm relative to the outer tube is effective to pull the linkage to move the inner tube relative to the outer tube.

4. The device of claim 3, wherein the linkage extends at an angle relative to a longitudinal axis of the outer tube to releasably lock the locking mechanism in the first position.

5. The device of claim 3, wherein the arm is effective to pull the linkage and inner tube in a proximal direction relative to the outer tube when the arm is moved from the first position to the second position.

6. The device of claim 1, wherein the distal end of the outer tube includes a lip formed thereon and configured to engage a corresponding groove formed in a bone anchor.

7. A bone anchor extension, comprising:
    an inner tube having proximal and distal ends with a lumen extending therebetween;
    an outer tube disposed about at least a portion of the inner tube, the outer tube having proximal and distal ends with a lumen extending therebetween, the outer tube being sized to span from at least a skin incision in a patient to a predetermined site proximate a spine of the patient; and
    a locking mechanism pivotally coupled to the inner and outer tubes and configured such that pivotal movement of the locking mechanism causes the distal end of the inner tube to move distally toward the distal end of the outer tube to engage a bone anchor therebetween;
    wherein the locking mechanism is movable between a first position, in which the locking mechanism extends longitudinally relative to a longitudinal axis of the outer tube, and a second position in which the locking mechanism extends transversely outward relative to a longitudinal axis of the outer tube;
    wherein the locking mechanism comprises an arm having at least one cam formed thereon and disposed between the inner and outer tubes; and
    wherein the at least one cam is pivotally coupled to the outer tube and is disposed within at least one cut-out formed in the inner tube such that pivotal movement of the arm is effective to move the inner tube relative to the outer tube.

8. The device of claim 7, wherein the inner tube includes opposed cut-outs formed in the proximal end thereof, and wherein pivotal movement of the arm between the first and second positions is effective to alter a size of the opposed cut-outs to thereby move the inner tube relative to the outer tube.

9. The device of claim 7, further comprising a locking mechanism formed on at least one of the arm and the outer tube and effective to releasably lock the arm in the first position.

10. The device of claim 9, wherein the locking mechanism comprises a plurality of teeth formed on the outer tube and adapted to engage the arm.

11. A spinal anchoring system, comprising:
    a bone anchor having a head with a bone-engaging shank extending therefrom; and
    a bone anchor extension having
        an inner tube having proximal and distal ends with a lumen extending therebetween,
        an outer tube disposed about at least a portion of the inner tube and having proximal and distal ends with a lumen extending therebetween, the outer tube being sized to span from at least a skin incision in a patient to a predetermined site proximate a spine of the patient, and a locking mechanism substantially external with respect to the outer tube, the locking mechanism having a proximal portion pivotally coupled to the outer tube and a distal portion pivotally coupled to the inner tube to pivot to move the inner tube distally toward the distal end of the outer tube to engage the head of bone anchor therebetween, wherein the locking mechanism is movable between a first position, in which the locking mechanism extends longitudinally relative to a longitudinal axis of the outer tube and the proximal portion is positioned on one side of the outer tube and the distal portion is positioned on an opposite side of the outer tube, and a second position in which the locking mechanism extends transversely outward relative to a longitudinal axis of the outer tube.

12. The system of claim 11, wherein the locking mechanism comprises an arm pivotally coupled to the outer tube and a linkage pivotally coupled between the arm and the inner tube.

13. The system of claim 12, wherein pivotal movement of the locking mechanism is adapted to pull the linkage proximally to move the inner tube proximally relative to the outer tube.

14. The system of claim 11, wherein the locking mechanism is coupled to a proximal end of the outer tube.

15. The system of claim 11, the head of the bone anchor includes a groove formed therein, and wherein the outer tube includes a lip formed on an inner surface of the distal end thereof for engaging the groove in the head.

16. A surgical method, comprising:
engaging a head of a bone anchor with a distal end of an outer tube; and
pivoting a locking mechanism pivotally coupled to a proximal portion of the outer tube at a proximal portion of the locking mechanism and to a proximal portion of an inner tube disposed within the outer tube at a distal portion of the locking mechanism to move the locking mechanism from an unlocked position to a locked position and thereby slide the inner tube distally toward the outer tube to engage the head of the bone anchor between the distal ends of the inner and outer tubes, wherein in the locked position the proximal portion of the locking mechanism is positioned on one side of the outer tube and the distal portion of the locking mechanism is positioned on an opposite side of the outer tube.

17. The method of claim 16, further comprising implanting the bone anchor in bone.

18. The method of claim 17, further comprising positioning a spinal fixation element within the head of the bone anchor, inserting a fastening element through the extension device, and mating the fastening element to the head of the bone anchor to lock the spinal fixation element within the head of the bone anchor.

19. The method of claim 16, further comprising moving the locking mechanism from the locked position to the unlocked position to release the head of the bone anchor from the distal ends of the inner and outer tubes.

20. The method of claim 16, wherein the locking mechanism includes a cam that moves the inner tube relative to the outer tube.

21. The method of claim 16, wherein the locking mechanism includes a hinge that moves the inner tube relative to the outer tube.

* * * * *